Figure 1:
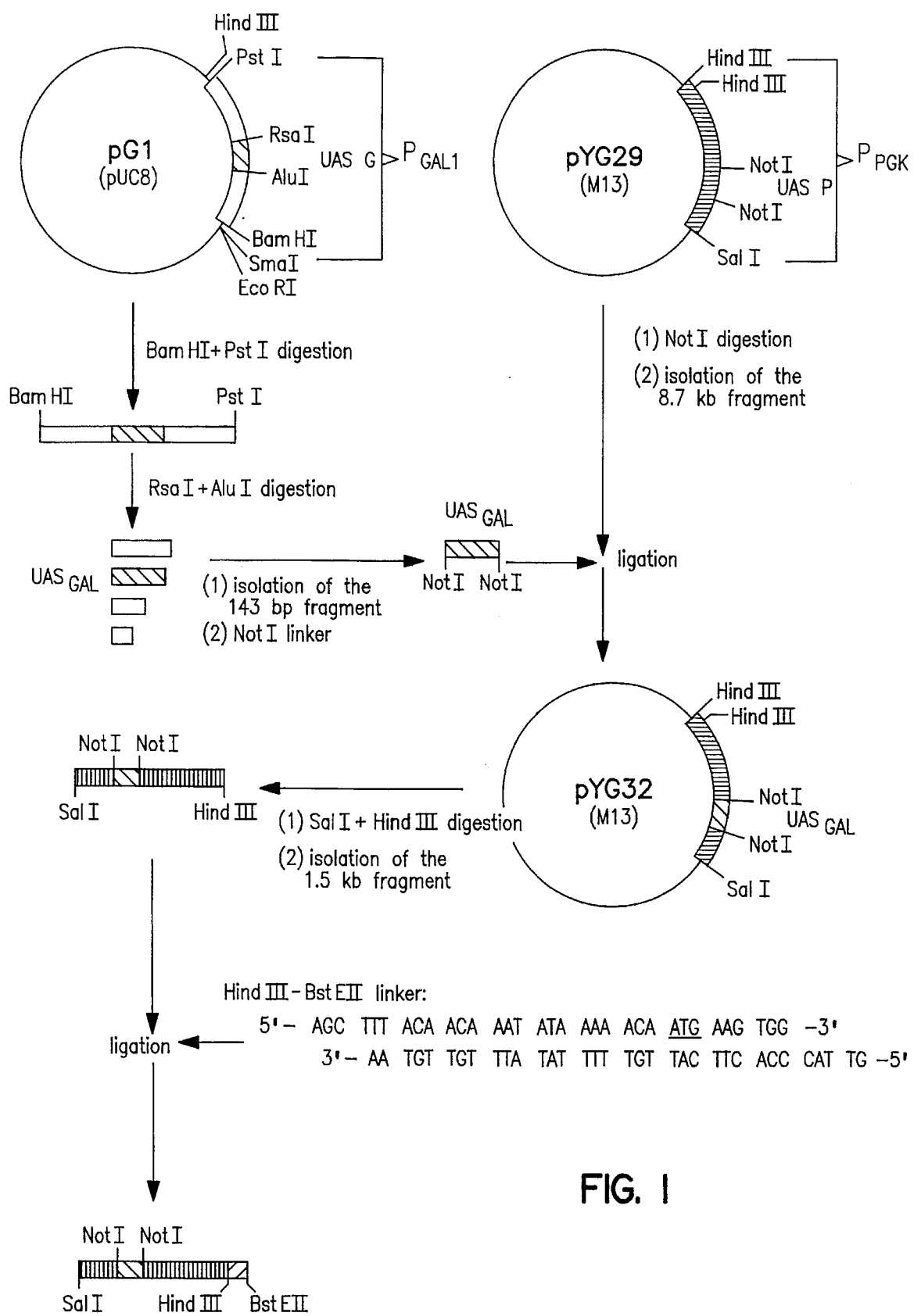

United States Patent [19]

Becquart et al.

[11] Patent Number: 5,612,196
[45] Date of Patent: Mar. 18, 1997

[54] HUMAN SERUN ALBUMIN, PREPARATION AND USE

[75] Inventors: Jérôme Becquart, Paris; Reinhard Fleer, Bures sur Yvette; Gérard Jung, Montlhery, all of France

[73] Assignee: Rhone-Poulenc Rorer S.A., Antony, France

[21] Appl. No.: 256,966

[22] PCT Filed: Jan. 26, 1993

[86] PCT No.: PCT/FR93/00072

§ 371 Date: Jul. 27, 1994

§ 102(e) Date: Jul. 27, 1994

[87] PCT Pub. No.: WO93/15204

PCT Pub. Date: Aug. 5, 1993

[30] Foreign Application Priority Data

Jan. 27, 1992 [FR] France ................................ 92 00807

[51] Int. Cl.$^6$ ........................ C12N 15/09; C12N 15/14; C12N 1/19; C07K 14/765
[52] U.S. Cl. ................. 435/69.6; 435/69.8; 435/172.3; 435/252.3; 435/254.2; 435/320.1; 530/363; 530/364; 514/8; 514/12
[58] Field of Search .................... 530/363, 364; 435/69.6, 69.8, 172.3, 252.3, 254.2, 320.1; 514/8, 12

[56] References Cited

U.S. PATENT DOCUMENTS

| 4,086,222 | 4/1978 | Lindquist et al. | 530/364 |
| 4,097,473 | 7/1978 | Lewis et al. | 530/364 |
| 5,330,901 | 7/1994 | Prevatt et al. | 435/69.6 |

FOREIGN PATENT DOCUMENTS

| 361991 | 4/1990 | European Pat. Off. . |
| 464590 | 1/1992 | European Pat. Off. . |

*Primary Examiner*—Robert A. Wax
*Assistant Examiner*—Rebecca Prouty
*Attorney, Agent, or Firm*—Julie K. Smith; Martin F. Savitzky

[57] ABSTRACT

The present invention relates to a preparation of serum-human albumin having a colorimetry index lower than 0.2 resulting from the expression, in a eukaryotic or prokaryotic host, of an exogenous DNA sequence.

11 Claims, 17 Drawing Sheets

OLIGODEOXYNUCLEOTIDES

Adaptor 1

A 5' CGTCGACACGCGTGCGCGCCCGCGGCCAATGGGGCCC 3'

B 5' TCGAGGGCCCCATTGGCCGCGGGCGCGCACGCGTGTCGACGAGCT 3'

Adaptor 2

C 5' AATTAGGCCAATGGGGCCGACGTCGCATGCGGCGCCGAGCT 3'

D 5' CGGCGCCGCATGCGACGTCGGCCCCATTGGCCT 3'

Adaptor 3

E 5' AATTCCCCGCGCGCCCATCGATCCGCTAGCCCACGCGTCCA 3'

F 5' GATCTGGACGCGTGGGCTAGCGGATCGATGGGCGCGCGGGG 3'

HUMAN SERUN ALBUMIN, PREPARATION AND USE

The present invention relates to a preparation of human serum albumin, a process for producing it, and its uses.

Human serum albumin (HSA) is a non-glycosylated monomeric protein of 585 amino acids, of a molecular weight of 66 KD. Its globular structure is maintained by 17 disulphide bridges which create a sequential series of 9 double loops (Brown, J. R., "Albumin Structure, Function and Uses", Rosenoer, V. M. et al. (eds.) Pergamon Press, Oxford, (1977) 27–51). The genes encoding HSA are known to be highly polymorphic, and more than 30 apparently different genetic variants have been identified by electrophoretic analysis under various conditions (Weitkamp, L. R. et al., Ann. Hum. Genet. 37 (1973) 291–226). The gene for HSA is cut in 15 exons by 14 intron sequences and comprises 16,961 nucleotides, from the supposed "capping" site up to the first site for addition of poly(A).

Human albumin is synthesized in the liver hepatocytes and then secreted in the blood stream. This synthesis leads, in a first instance, to a precursor, prepro-HSA, which contains a signal sequence of 18 amino acids directing the nascent polypeptide in the secretory pathway.

HSA is the most abundant protein in the blood, with a concentration of about 40 g per liter of serum. There are therefore about 160 g of albumin circulating in the human body at any time. The most important role of HSA is to maintain a normal osmolarity of the blood stream. It also has exceptional binding capacity for various substances and plays a role both in the endogenous transport of hydrophobic molecules (such as steroids and bile salts) and in that of various therapeutic substances which can also be transported to their respective sites of action. Furthermore, HSA has recently been implicated in the catabolism of prostaglandins.

HSA represents 40% of the world market for plasma proteins. Its commercial interest lies in the fact that this product is widely used, for example in so called replacement solutions to compensate for blood losses during surgical procedures, accidents or haemorrhages, and at doses which may be as high as several tens of grams per day per individual. Currently, the annual consumption of HSA can be estimated at more than 300 tonnes.

Up until now, the HSA available on the market is produced by purification from biological material of human origin. In particular, it is obtained by conventional techniques for fractionation of plasma obtained from blood donations (Cohn et al., J. Am. Chem. Soc. 68 (1946) 459 pp), or by extraction from human placenta, according to the technique described by J. Liautaud et al. (13th International Congress of IABS, Budapest; A: "Purification of proteins. Development of biological standard", Karger (ed), Bale, 27 (1973) 107 pp).

The development of genetic engineering and new extraction and purification techniques has opened the possibility of obtaining, at a lower cost price, improved products of higher purity, of better stability and without risk of viral contamination (for example hepatitis B and AIDS). Given the importance of the HSA market, the possibility of producing this protein by the recombinant route has been widely studied. Thus, numerous expression systems have been studied for the preparation of recombinant HSA.

More particularly, as regards bacterial hosts, the first genetic engineering experiments used the bacterium *E. coli* as host organism. Thus, European Patents EP 236 210, EP 200 590, EP 198 745 or EP 1 929 describe processes for the production of HSA in *E. coli* using various expression vectors, various transcriptional promoters, and various signals for secretion. Subsequently, work relating to the secretion of HSA in *Bacillus subtilis* was also carried out, even though the levels of albumin obtained in this system still do not appear to be satisfactory (Saunders et al., J. Bacteriol. 1.69 (1987) 2917).

As regards the eucaryotic hosts, processes for the production of HSA have been developed using yeasts as host organism. Thus, it has been possible to demonstrate in *S. cervisiae* (Etcheverry et al., Bio/Technology 4 (1986) 726) the secretion of HSA directed by its own signal peptide under the control of the chelatin promoter. The production of HSA has also been mentioned in the brewery yeast during the manufacture of beer, using a post-fermentation process (EP 201 239). More recently, Patent Application EP 361 991 describes a particularly efficient system using the yeast Kluyveromyces as host organism, transformed with vectors derived from the plasmid pKD1. It was possible to obtain particularly high levels of secreted HSA in the culture medium with this system. Finally, the production of recombinant HSA has also been described in *Pichia pastoris* (EP 344 459). In addition, the purification of HSA has also been the subject of numerous studies (EP 319 067).

Yet, in spite of major efforts devoted to the production of HSA by the recombinant route, this product is still not present on the market. This is linked to the difficulty of developing a fairly efficient process based on genetic engineering, which makes it possible to obtain, on the industrial scale and under economically profitable conditions, a HSA which can be used pharmaceutically. In particular, While the questions of productivity appear to be more or less resolved (production at high levels of a correctly matured, secreted albumin possessing a tertiary structure conforming to that of native human serum albumin), the processes described in the prior art do not make it possible to obtain a HSA which can be used pharmaceutically. It is indeed essential that the HSA produced conforms to certain qualitative standards. In particular, given its pharmaceutic use, the recombinant HSA should possess the physico-chemical properties of native albumin and meet certain criteria of homogeneity, purity and stability. Thus, the pharmacopoeia sets a certain number of parameters for solutions of plasma albumAn, namely a pH value, a protein content, a content of polymers and aggregates, a content of alkaline phosphatase, of potassium and of sodium and a certain protein composition. It also requires a certain absorbance, the conformity with a test of sterility, with an assay for pyrogens and for toxicity (see "Albumini humani solutio" European pharmacopoeia (1984) 255).

One of the major problems of the processes of the prior art involving genetic engineering techniques, is that they generate a coloured recombinant HSA. This phenomenon is most particularly important in the case of systems permitting the expression and secretion of recombinant HSA in the culture medium. In this respect, Examples B1 and B2 of the present application illustrate the problem of coloration in the case of an expression system using, under the conditions of the prior art, a yeast as host organism. Example B1 is not restrictive but illustrates a coloration phenomenon which was observed for all the strains tested, regardless of the mode of fermentation adopted (fed-batch, batch, continuous). Moreover, in spite of the numerous efforts made to this end, it has never been possible to remove this coloration by purification (see Example B2). Under these conditions, no HSA produced by the recombinant route has ever been described in the prior art lacking this coloration. Yet, the presence of this coloration constitutes an obstacle to the pharmaceutical exploitation of recombinant HSA. Indeed, the products thus obtained are heterogeneous since they comprise the components responsible for the coloration. Furthermore, their composition is undefined since the coloration can vary from one preparation to another and that the prior art does not make it possible to control this coloration. Under these conditions, it is very difficult to define a reproducible process which makes it possible to obtain, each time, identical preparations of recombinant HSA. Finally, because of the presence of components responsible for the coloration, the recombinant HSA of the prior art is potentially immunogenic.

One of the aspects of the invention is to provide a preparation of recombinant HSA of good quality, possessing the properties of extracted HSA, and which can be used in the pharmaceutical field.

In particular, one aspect of the invention is to provide a preparation of recombinant HSA possessing, after purification by known methods (concentration, precipitation, chromatography and the like), a colorimetry index of less than 0.2. For the purposes of the present invention, colorimetry index is understood to mean the ratio of the absorbance at 300 nm to the absorbance at 280 nm (i=$OD_{300}/OD_{280}$). This ratio characterizes particularly well the colorimetry for HSA since it reflects, for a given solution, its absorbance independently of its concentration.

One objective of the invention is to permit the production, in industrial quantities and at an economically profitable level, of a preparation of recombinant HSA which can be used pharmaceutically.

The applicant has now shown that it is possible to obtain a non-coloured HSA solution in industrial quantities by the recombinant route. The present invention rests on the demonstration that the quality of the HSA produced is not only linked to the host or to the chosen vector, or to the process for the purification of HSA from the medium, but to a large extent to the very composition of the production medium. Thus, by modifying especially the carbon sources and the conditions for preparing the production medium, it was possible to obtain recombinant HSA solutions having a colorimetry index of less than 0.2.

A first subject of the invention therefore lies in a human serum albumin characterized in that it possesses a colorimetry index of less than 0.2 and in that it results from the expression, in a eucaryotic or procaryotic host, of an exogenous DNA sequence.

The present invention provides, for the first time, a recombinant HSA having a colorimetry index of less than 0.2. It thus provides a recombinant HSA which can be used in the pharmaceutical field, with very low risks of immunogenic reactions. Furthermore, compared with plasma HSA, the HSA of the invention offers the advantage of being homogeneous and of perfectly defined composition. Indeed, because of its polymorphism, numerous HSA variants exist. Thus, among those which have been identified, some variants conserve a substituted pro peptide (Brennen and Carrell, Nature 274 (1978) 908; Galliano et al., Rev. Fr. Transfus. Immuno-Hématol. 27 (1984) 597), others possess point mutations (Winter et al., Biochemistry 11 (1972) 889; Franklin et al., Proc. Natl. Acad. Sci. U.S.A 77 (1980) 2505; Brennen, Biochim. Biophys. Acta 830 (1985) 320; Galliano et al., Protides Biol. Fluids Proc. Colloq. 34 (1986) 815; Takahashi et al., J. Chromatogr. 359 (1986) 181) or deletions at the C-terminal end (Galliano et al., J. Biol. Chem. 261 (1986) 4283). Furthermore, there are many variants for which structural changes have not been identified. Because of this, the plasma HSA obtained by extraction of biological material derived from a very large number of human donors potentially contains all the HSA variants resulting from its polymorphism. The present invention provides a homogeneous and defined HSA, because of its preparation by the genetic route, by expression of one or more identified DNA sequences.

Preferably, the HSA of the present invention has a colorimetry index of less than 0.15.

Still more preferably, the HSA of the present invention has a colorimetry index of less than 0.1.

Other physico-chemical characteristics of the HSA of the present invention are given in Example B5, namely especially its fluorescence spectrum. All these parameters demonstrate the quality of the HSA of the invention.

For the purposes of the present invention, exogenous DNA sequence is understood to mean any DNA sequence introduced artificially into the host used and encoding HSA. In particular, it may be, depending on the host, genomic sequences, cDNA, hybrid sequences and the like. For a better implementation of the invention, the use of a cDNA is however preferred. Such sequences have already been described in the prior art (cf especially EP 361 991 and Dugaiczyk et al., J. Supramol. Struct. & Cell Biochem., Suppl. 5 (1981)). Moreover, this exogenous DNA generally comprises a region for initiation of transcription and translation joined to the 5 terminal end of the coding sequence, so as to direct and regulate the transcription and translation of the said sequence. The choice of these promoter regions may vary according to the host used.

Within the framework of the present invention, the exogenous DNA is preferably part of a vector, which may be one affording autonomous or integrarive replication. More particularly, autonomously replicating vectors can be prepared using autonomously replicating sequences in the chosen host. As example, in yeast, this may be replication origins derived from plasmids: pKD1 (EP 241 435), 2μ (Beggs, Nature 275 (1978) 104–109), and the like; or alternatively chromosomal sequences (ARS). As regards integrarive vectors, these can be prepared for example using sequences homologous to certain regions of the host genome, which permit, by homologous recombination, the integration of the vector. In this respect, the use of rDNA permits a multiple integration of the exogenous DNA, and therefore its presence in higher copy number per cell.

In a preferred mode, the HSA of the invention results from the expression, in an eucaryotic or procaryotic host, of an exogenous DNA sequence and from the secretion of the expression product of the said sequence into the culture medium. It is indeed particularly advantageous to be able to obtain, by the recombinant route, a HSA of pharmaceutical quality directly in the culture medium. In this case, the exogenous DNA sequence comprises, upstream of the sequence encoding HSA, or, where appropriate, between the region for initiation of transcription and translation and the coding sequence, a "leader" sequence directing the nascent protein in the secretory pathways of the host used. This "leader" sequence may be the natural "leader" sequence of HSA, but it may also be a heterologous sequence (derived from a gene encoding another protein) or even artificial. The choice of one of these sequences is especially guided by the host used. As example, when the host used is a yeast, it is possible to use, as heterologous "leader" sequence, that of the pheromone factor α, invertase or acid phosphatase.

Among the eucatyotic hosts which can be used within the framework of the present invention, there may be mentioned animal cells, yeasts or fungi. In particular, as regards yeasts, there may be mentioned yeasts of the genus Saccharomyces, Kluyveromyces, *Pichia pastoris*, Schwanniomyces or Hansenula. As regards animal cells, there may be mentioned COS, CHO and C127 cells and the like. Among the fungi capable of being used in the present invention, there may be mentioned more particularly Aspergillus ssp. or Trichoderma ssp.

As procaryotic hosts, the use of the following bacteria *E. coli*, Bacillus or Streptomyces is preferred.

Another subject of the invention relates to a process for preparing HSA having a colorimetry index of less than 0.2 according to which the following steps are carried out:

in a first step, an exogenous DNA encoding the human serum albumin under the control of transcriptional and translational signals appropriate to the host used is introduced into a eucaryotic or procaryotic host cell, in a second step, the cell thus obtained is cultured in a medium of defined composition containing at least one carbon source chosen from alcohols, non-reducing sugars, organic acids or glucose derivatives substituted on the oxygen of the carbon C4; or in a medium prepared so as to remove or limit the formation of aldehyde type impurities, and, in a third step, the HSA produced is recovered.

More particular, during the first step of the process of the invention, the exogenous DNA can be introduced into the host cell by various techniques. Especially, the introduction can be carried out by transformation, conjugation or electroporation.

As regards the transformation, various procedures have been described in the prior art. In particular, it can be carried out by treating the whole cells in the presence of lithium acetate and polyethylene glycol according to the technique described by Ito et al. (J. Bacteriol. 153 (1983) 163–168), or in the presence of ethylene glycol and dimethyl sulphoxide according to the technique of Durrens et al. (Curr. Genet. 18 (1990) 7). An alternative procedure has also been described in Patent Application EP 361 991. More specifically, for the procaryotic cells, the transformation can be carried out according to the technique described by Dagert et al. (Gene 6 (1979) 23–28) by treating with a solution of $CaCl_2$ followed by heat shock. For animal cells, it can also be carried out by the calcium phosphate technique according to Haynes (Nucleic Acids Res., 11 (1983) 687–706).

As regards electroporation, the technique described by Karube et al. (FEBS Letters 182 (1985) 90) can be advantageously used.

The choice of either of these methods is established especially as a function of the host chosen and the exogenous DNA used.

Among the eucaryotic hosts which can be used in the process of the invention, there may be mentioned the animal cells, yeasts or fungi which were mentioned above. Among the procaryotic hosts, any bacterium defined above can be used.

In a preferred embodiment of the invention, the process is carried out using, as host cell, a eucaryotic cell.

Still more preferably, the process of the invention is carried out using, as host cell, a yeast.

The exogenous DNA encoding the HSA which can be used in the process is defined as above. Preferably, it is a cDNA, a genomic DNA or a hybrid DNA. For a better implementation of the invention, the use of a cDNA is however preferred. Moreover, this exogenous DNA generally comprises a region for initiation of transcription and translation joined to the 5' terminal end of the coding sequence, so as to direct and regulate the transcription and translation of the said sequence. The choice of this region may vary as a function of the host used.

In a particularly advantageous embodiment of the invention, the exogenous DNA comprises, upstream of the sequence encoding mature HSA, a "leader" sequence directing the nascent protein in the secretory pathways of the host used. Such sequences have been defined above. Moreover, within the framework of the present invention, the exogenous DNA is preferably part of a vector, which may be one affording autonomous or integrated replication, as indicated above.

In a preferred embodiment of the invention, the process of production is characterized in that the HSA is secreted into the control medium. It is indeed particularly advantageous to be able to obtain, by the recombinant route, a HSA of pharmaceutical quality directly from the control medium.

The second step of the process of the invention consists in culturing the recombinant cells under conditions permitting the expression of the exogenous DNA sequence encoding HSA. This step is particularly important since it directly influences the quantity and quality of the HSA produced. The present invention describes, for the first time, culture conditions which permit the production of a serum albumin of pharmaceutical qualities.

Among the alcohols which can be used in the process of the invention, there may be mentioned preferably simple alcohols containing at least two carbon atoms (ethanol and the like), or polyalcohols (glycerol, sorbitol and the like). As non-reducing sugars, there may be mentioned for example sucrose, and, as organic acids, acetates or lactates. The glucose derivatives which can be used in the present invention correspond more specifically to the following formula:

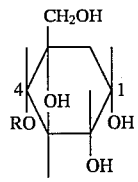

in which R is different from hydrogen. As example, there may be mentioned disaccharides, and preferably the disaccharides having a glycoside bond of the 1–4 type such as maltose, cellobiose or lactose.

It is understood that the choice of one or more of these compounds is guided by the host used. However, it is also possible to modify a host in order to render it capable of assimilating a preferred carbon source.

These various carbon sources can also be used separately or in combination. For example, the combination of a glucose derivative and an alcohol gives very good results. Likewise, the combination of a simple alcohol and a polyalcohol also gives an albumin of very high quality. In addition, an unexpected result is that this the of combination also makes it possible, in certain cases, to increase the levels of production of HSA, and therefore to improve the yields of the manufacturing process.

The process of the invention can also be implemented in a medium prepared so as to eliminate or limit the formation of aldehyde type impurities. This type of preparation is generally useless when one or more of the carbon sources listed above are used in a medium of defined composition. Various means can be used to limit the formation of such impurities, of which the choice depends on the medium (nature of the carbon source) and the host considered. As example, it may be advantageous to sterilize the carbon source at cold temperature (for example by filtration as illustrated in Example B4).

The third step of the invention makes it possible to extract, from the culture medium, the HSA produced. In the case where the HSA is secreted into the medium by the recombinant cells, this extraction can be carried out directly from the culture supernatent obtained by centrifugation. In the case where the HSA is not secreted, it is necessary, prior to the extraction, to break the cells in culture so as to liberate the HSA which they contain. This prior step can be carried out by various physical or physico-chemical means (sonication, grinding, osmotic shock, heat shock and the like).

The extraction can be carried out by various techniques known to a person skilled in the art and described in the literature. Generally, these techniques involve concentration, precipitation and chromatographic steps. Some of these various techniques are illustrated in the examples.

Another subject relates to any pharmaceutical composition comprising HSA as defined above.

The present invention will be more completely described with the aid of the following examples, which should be considered as illustrative and non-limiting.

LEGEND TO THE FIGURES

FIG. 1: Construction of the hybrid promoter PGK/GAL. P=promotery UAS="upstream activating sequence".

Figure 2:
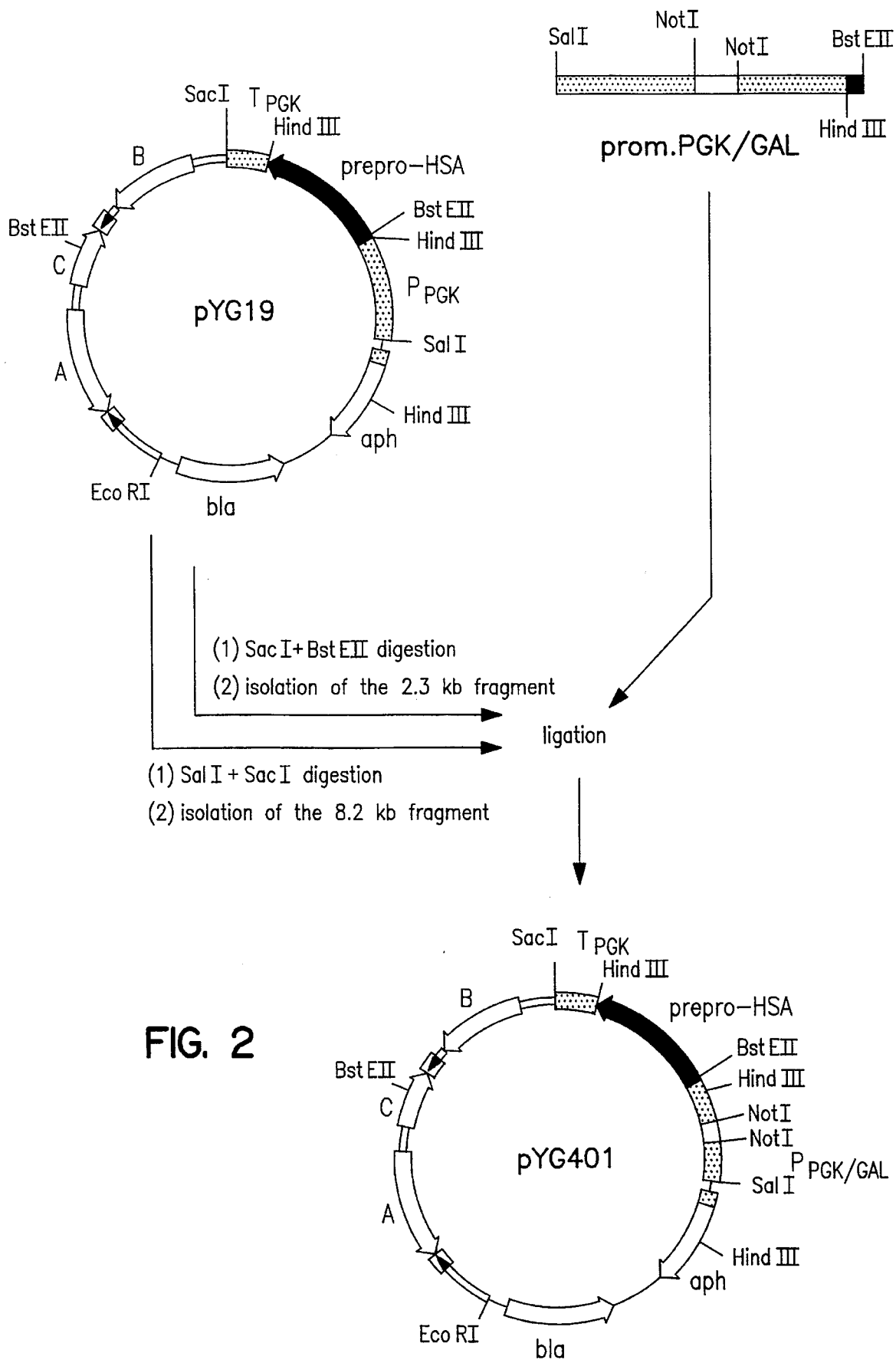

FIG. 2: Strategy for the construction and representation of the vector pYG401. P=promoter; T=transcriptional terminatory bla=gens conferring the resistance to ampicillin; aph= gene conferring the resistance to geneticin (G418).

Figure 3:
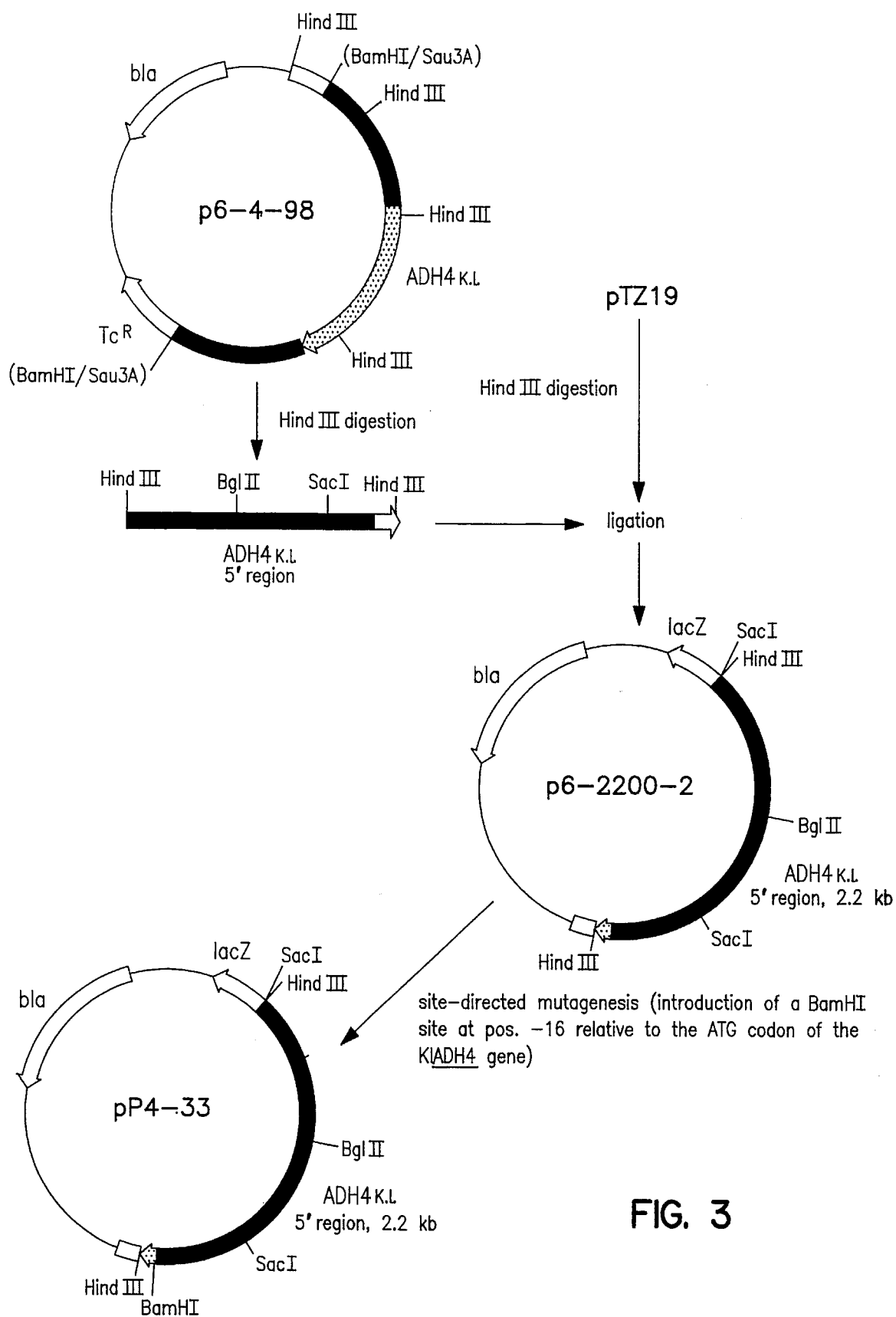

FIG. 3: Construction and representation of the plasmid pP4-33.

Figure 4:
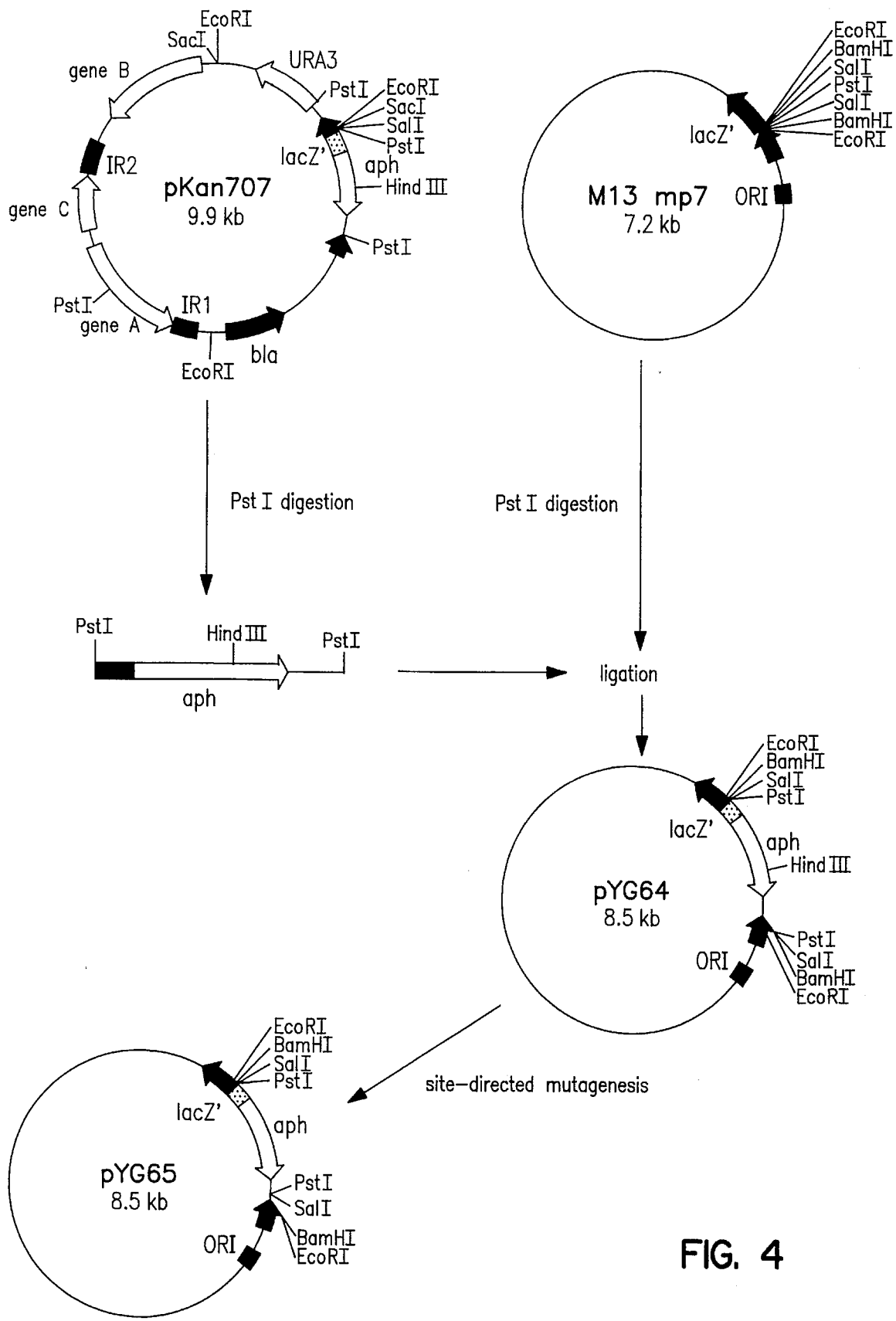

FIG. 4: Construction and representation of the plasmid pYG65.

Figure 5:
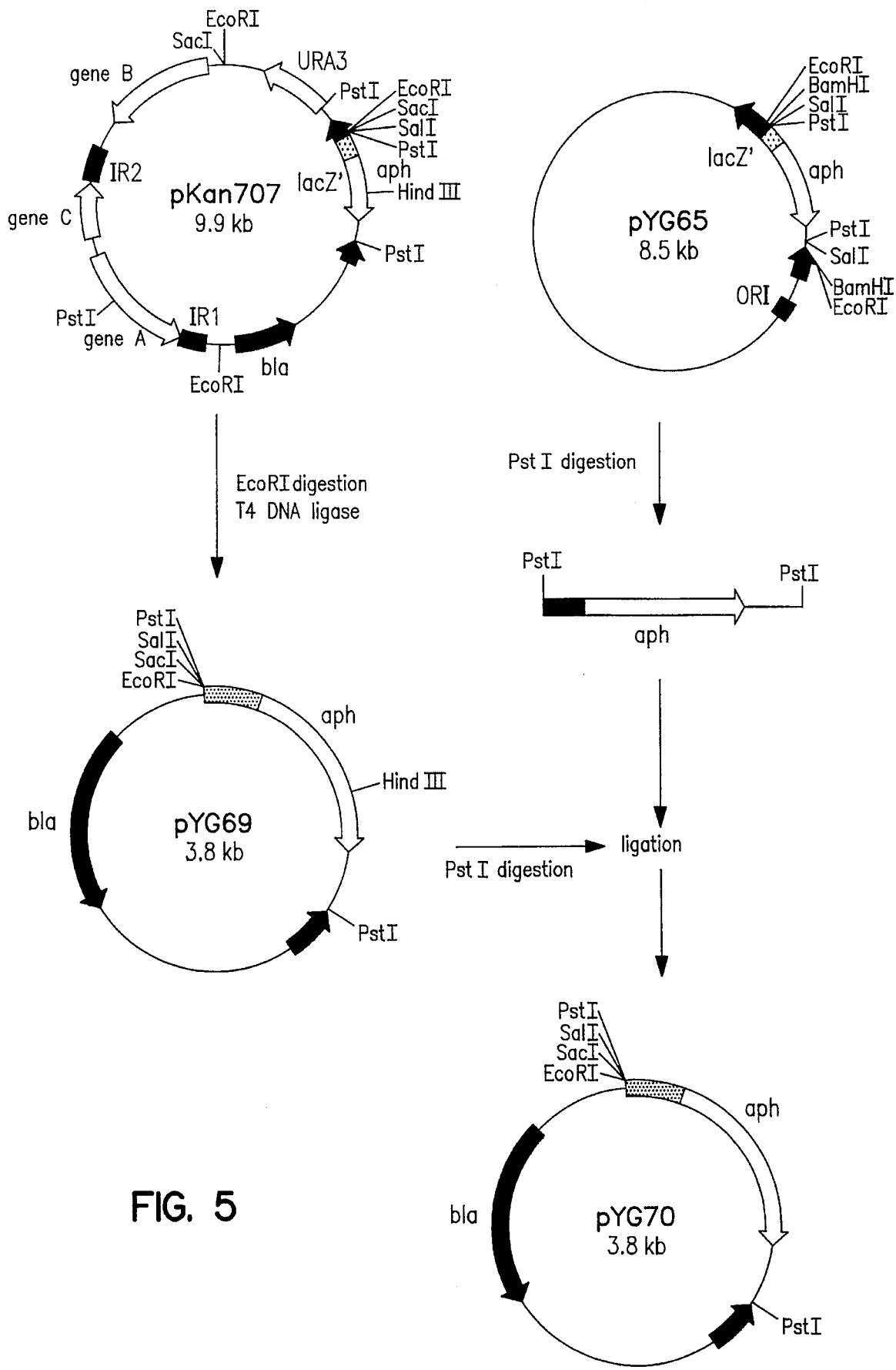

FIG. 5: Construction and representation of the plasmid pYG70.

Figure 6:
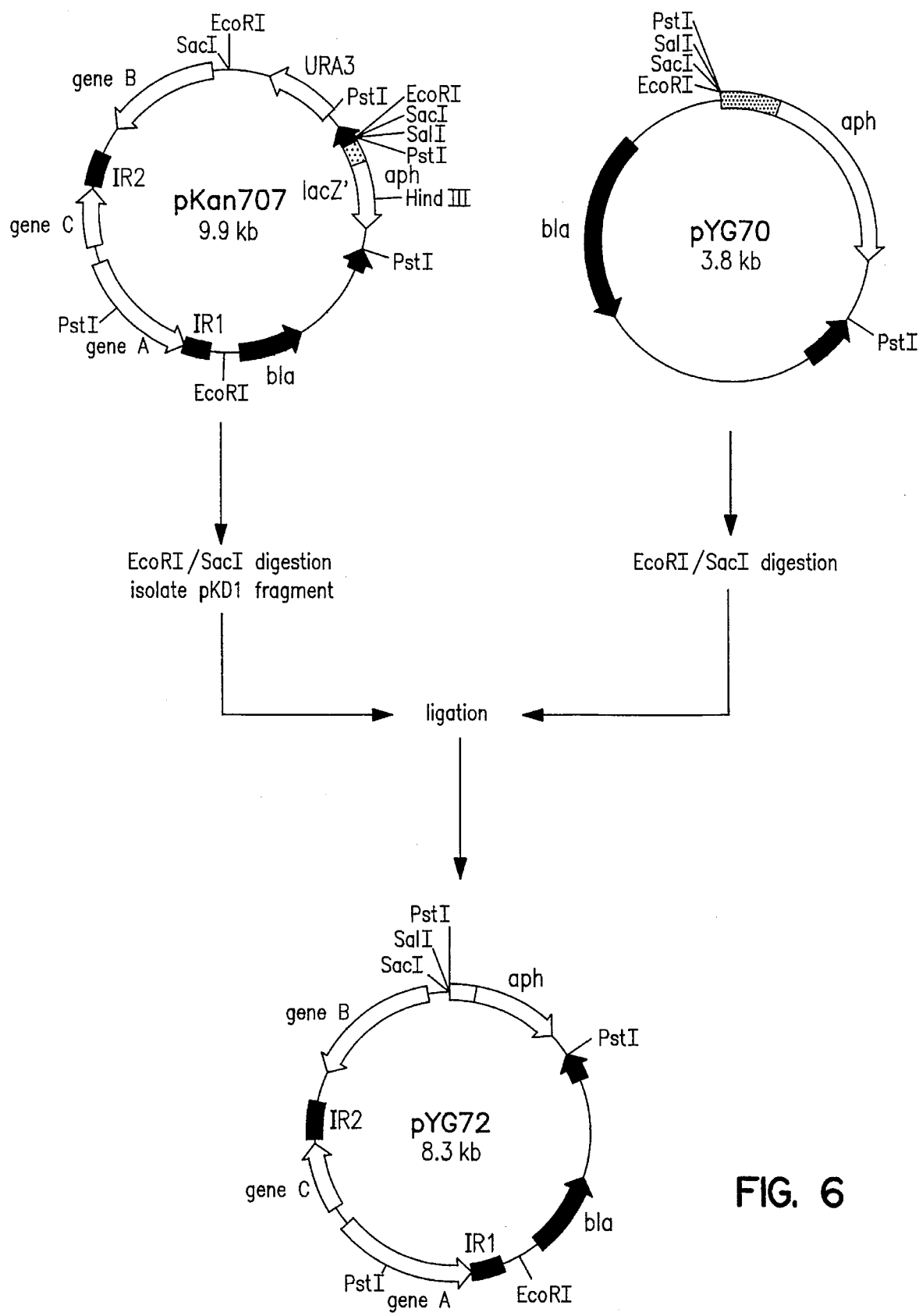

FIG. 6: Construction and representation of the plasmid pYG72.

Figure 7:
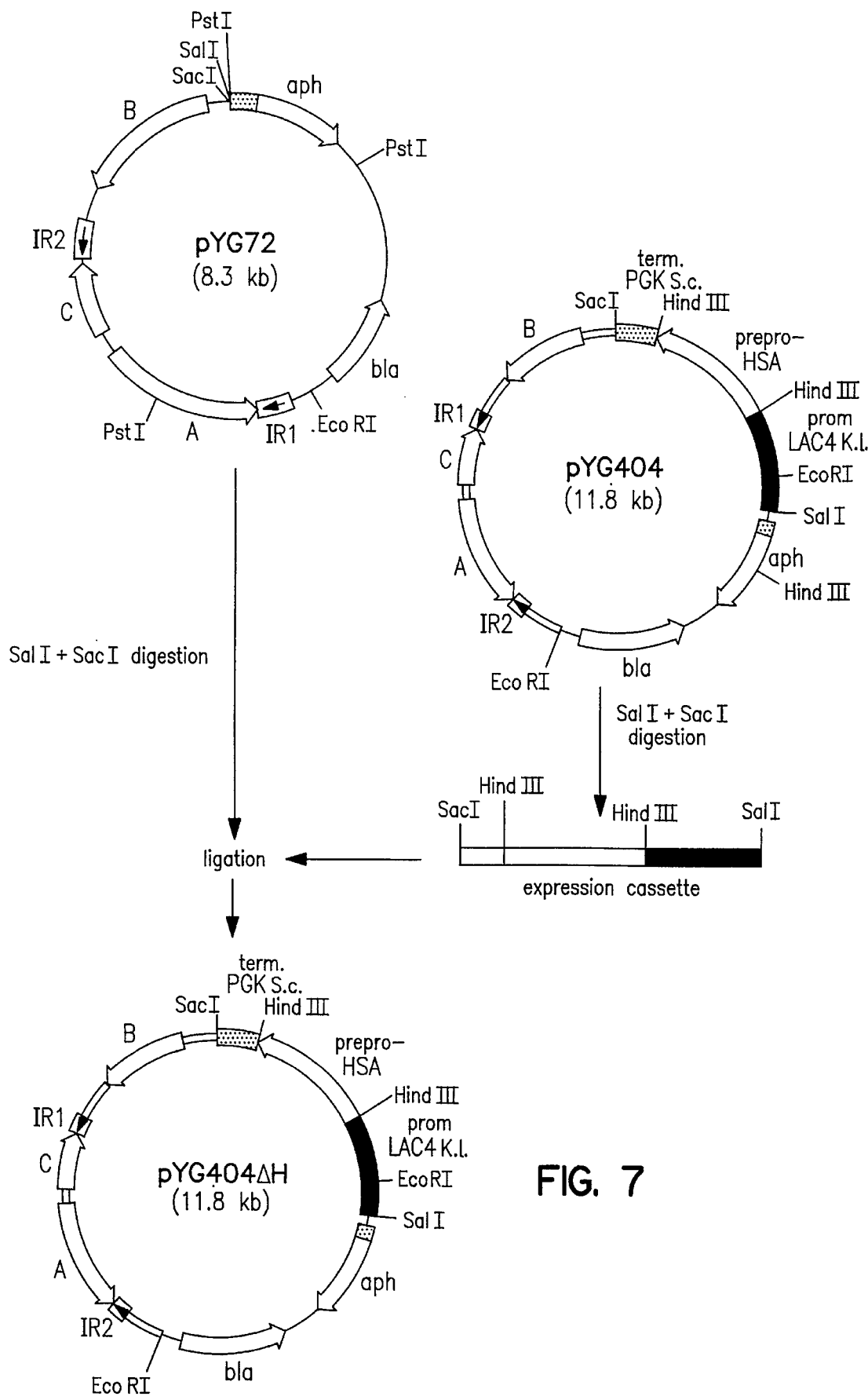

FIG. 7: Construction and representation of the plasmid pYG404ΔHindIII.

Figure 8:
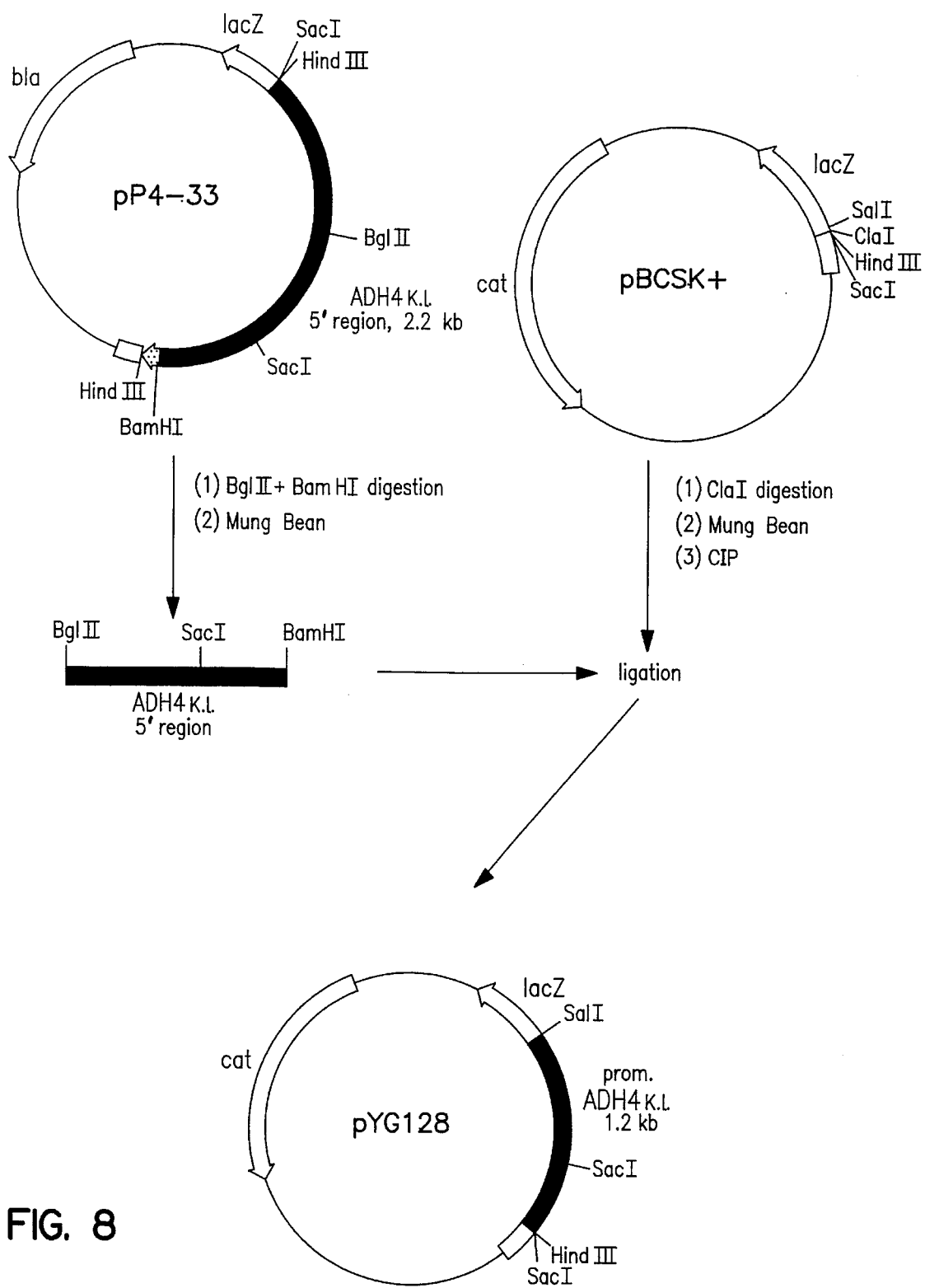

FIG. 8: Construction and representation of the plasmid pYG128.

Figure 9:
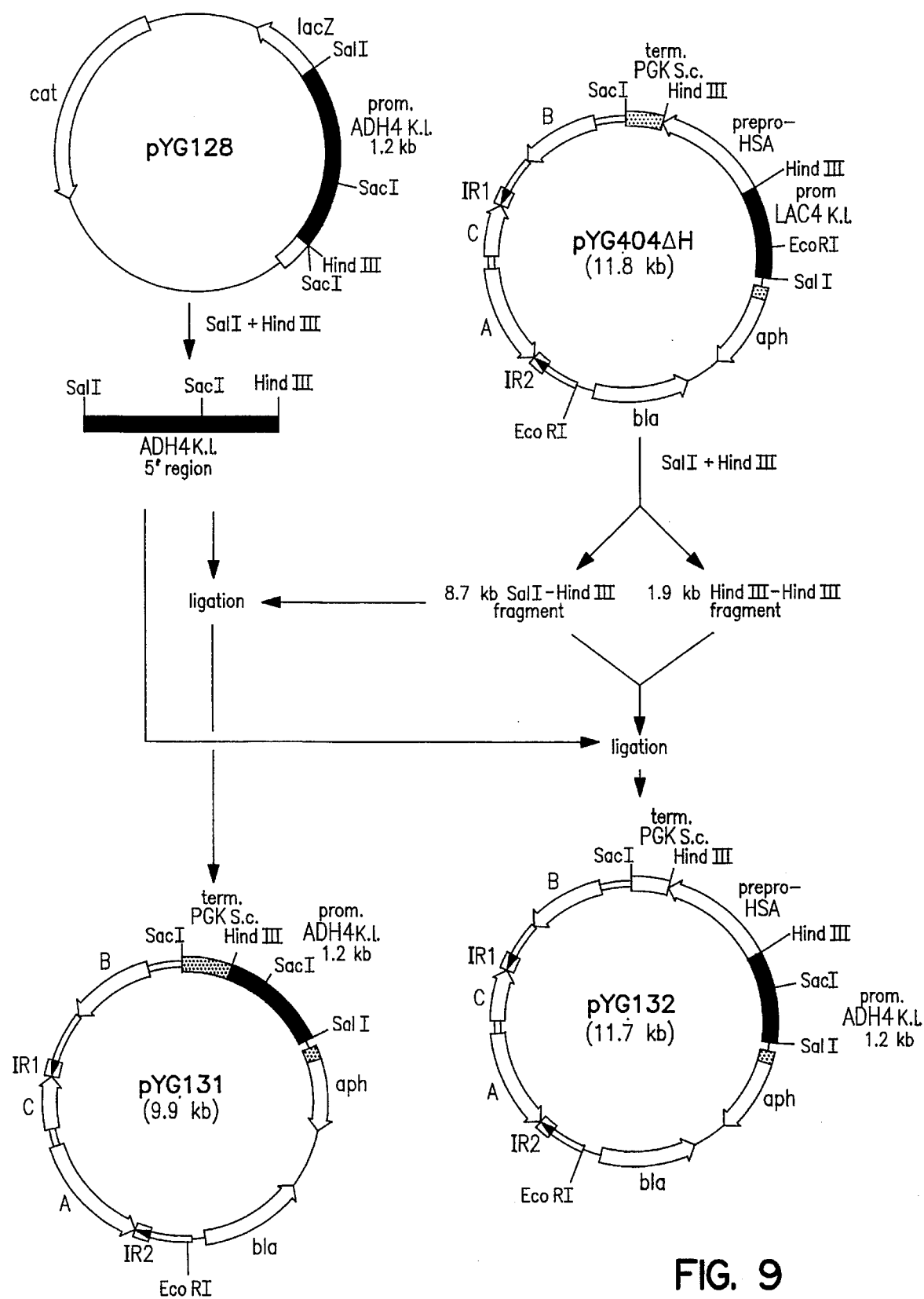

FIG. 9: Construction and representation of the plasmids pYG131 and pYG132.

Figures 10, 12:
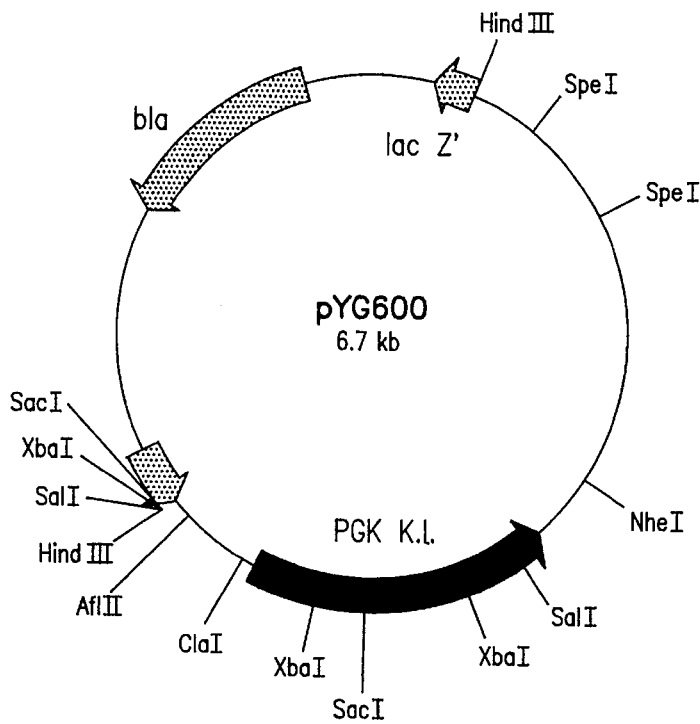

FIG. 10: Restriction map of the plasmid pYG600. bla= β-lactamase gene conferring the resistance to ampicillin.

Figure 11:
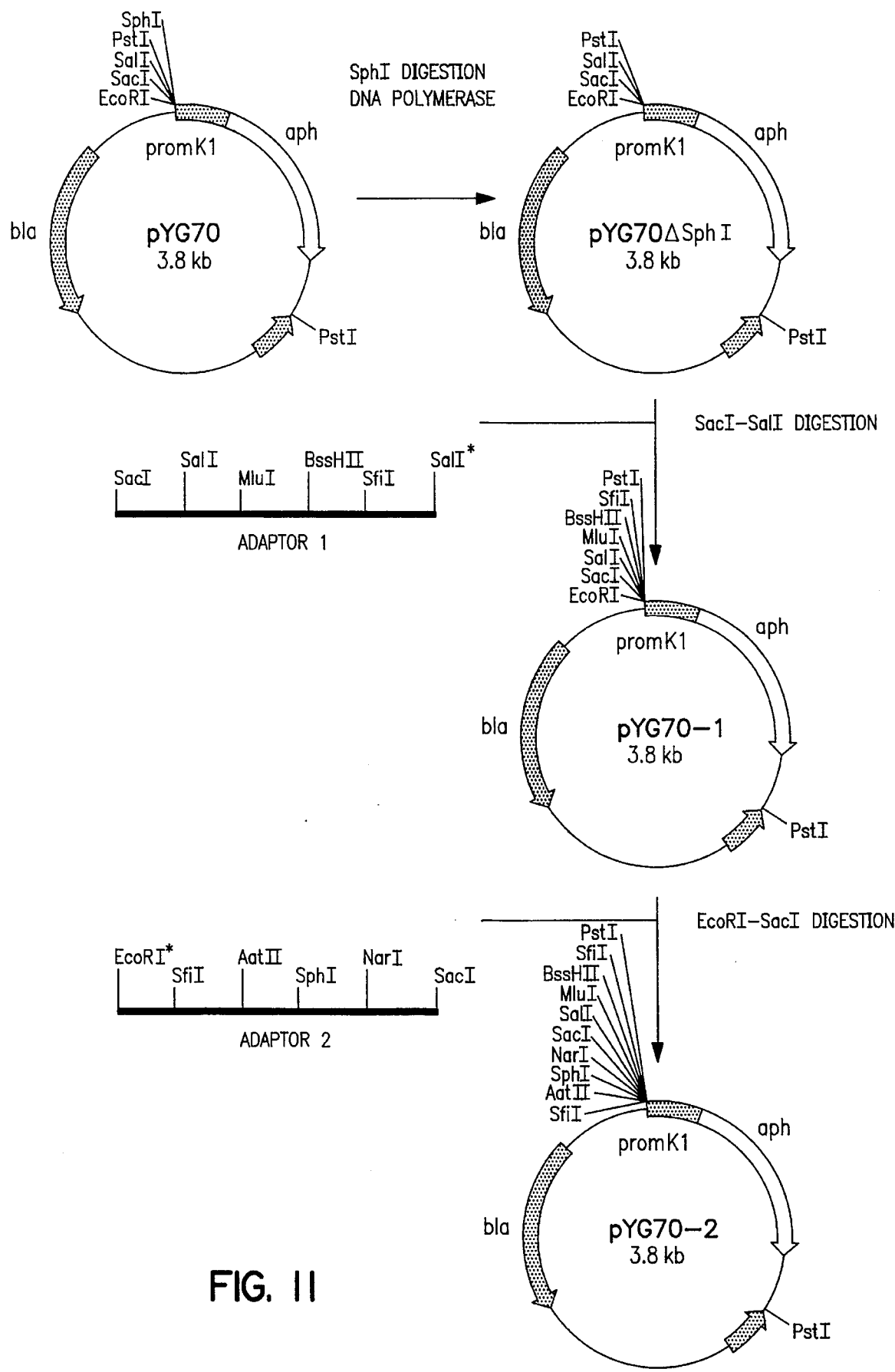

FIG. 11: Strategy for the construction of the plasmid pYG70-2. aph=3'-aminoglycoside phosphotransferase gene conferring the resistance to geneticin (G418); prom=promoter; IR=inverted repeat sequence; ORI=replication origin; LacZ'=β-galactosidase structural gene. The sites marked with an (*) possess ends compatible with the corresponding sites without reconstituting, after ligation, cleavage sites recognized by the said enzymes.

FIG. 12: Sequence of the synthetic oligodeoxynucleotides A-F having served for the construction of the adaptors 1 to 3.

Figure 13:
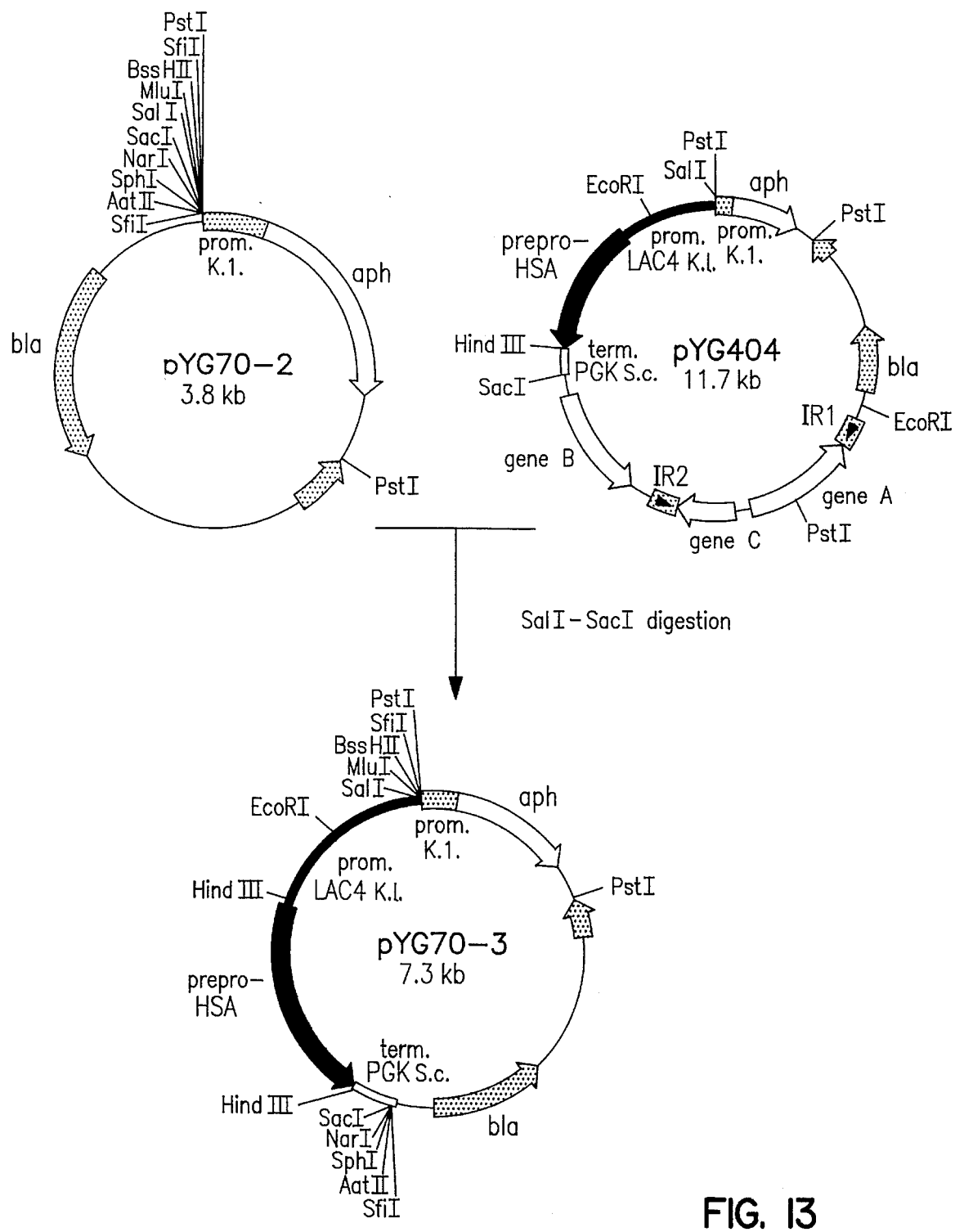

FIG. 13: Strategy for the construction of the plasmid pYG70-3. For the legend, see FIG. 11. term=terminator.

Figure 14:
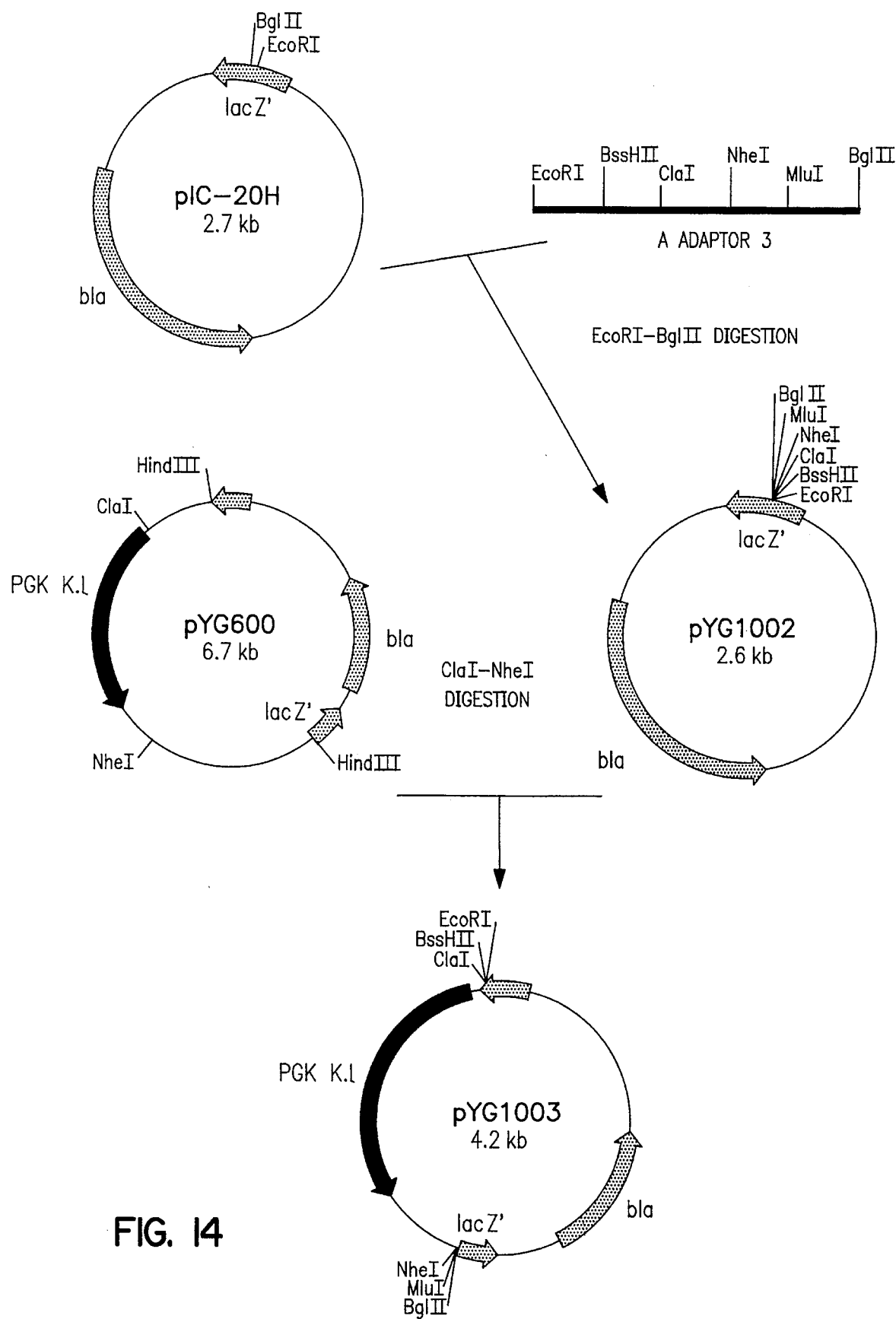

FIG. 14: Strategy for the construction of the plasmid pYG1003. For the legend, see FIG. 11.

Figure 15:
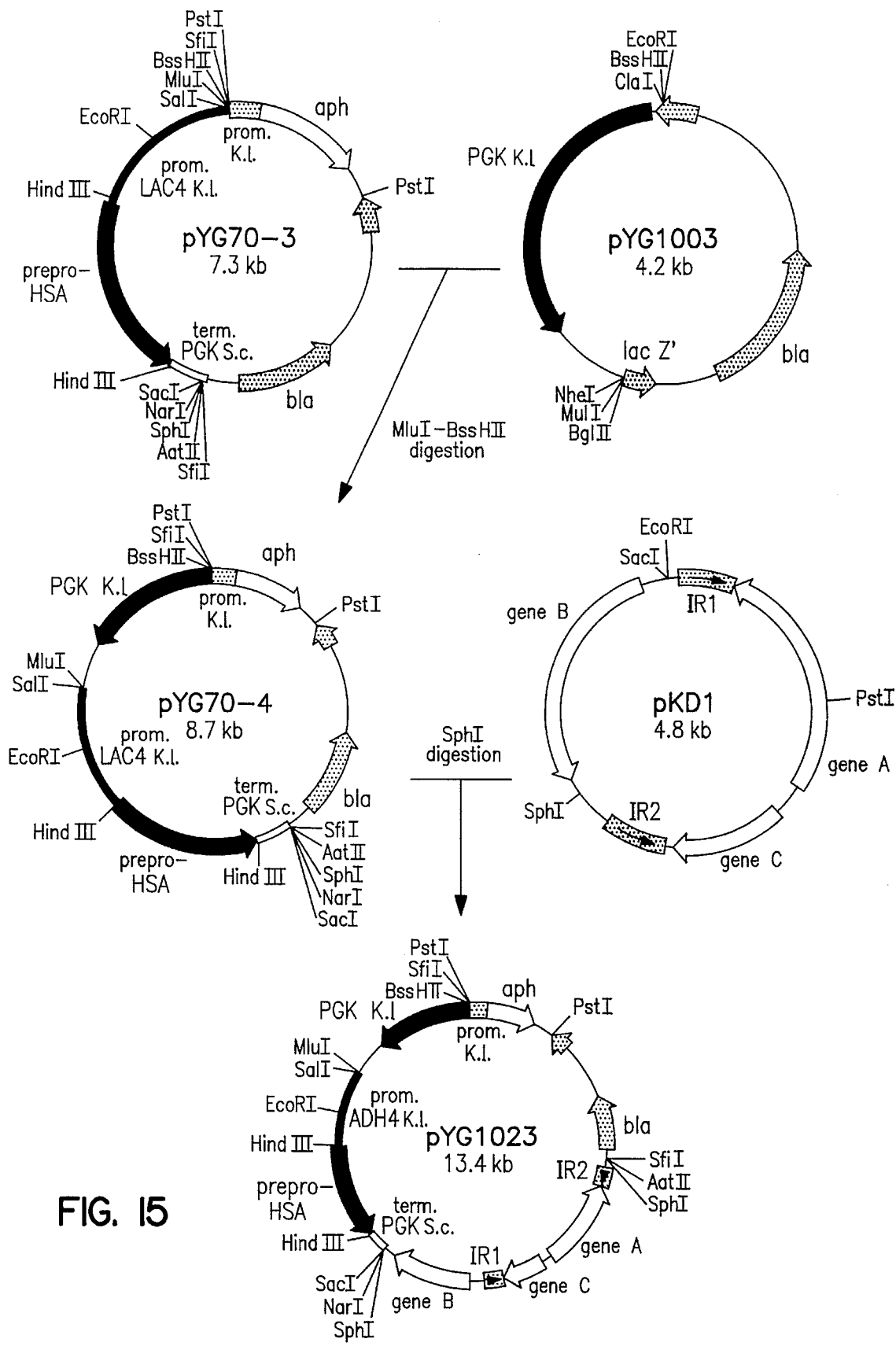

FIG. 15: Strategy for the construction of the plasmid pYG1023. For the legend, see FIG. 11.

Figure 16:
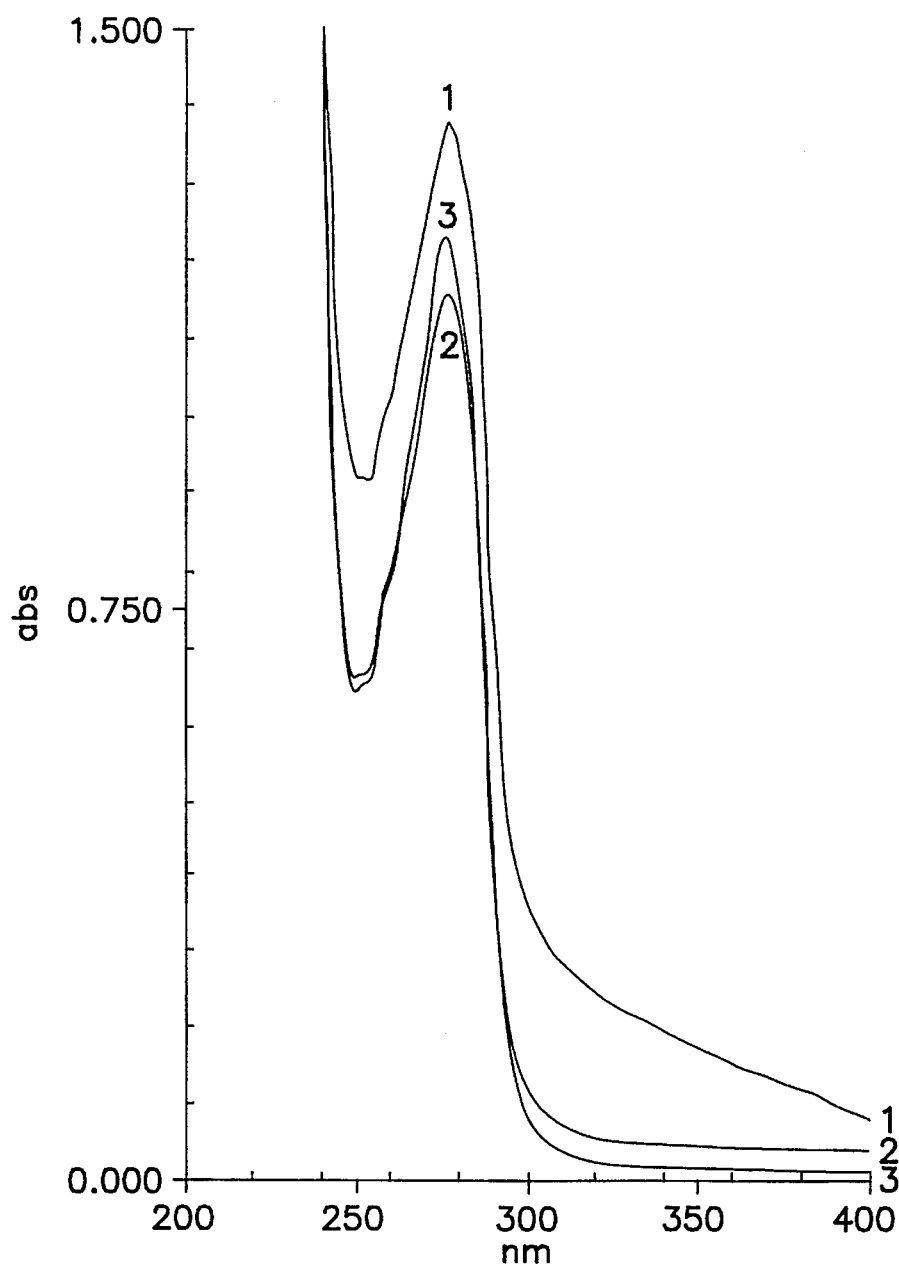
Figure 17:
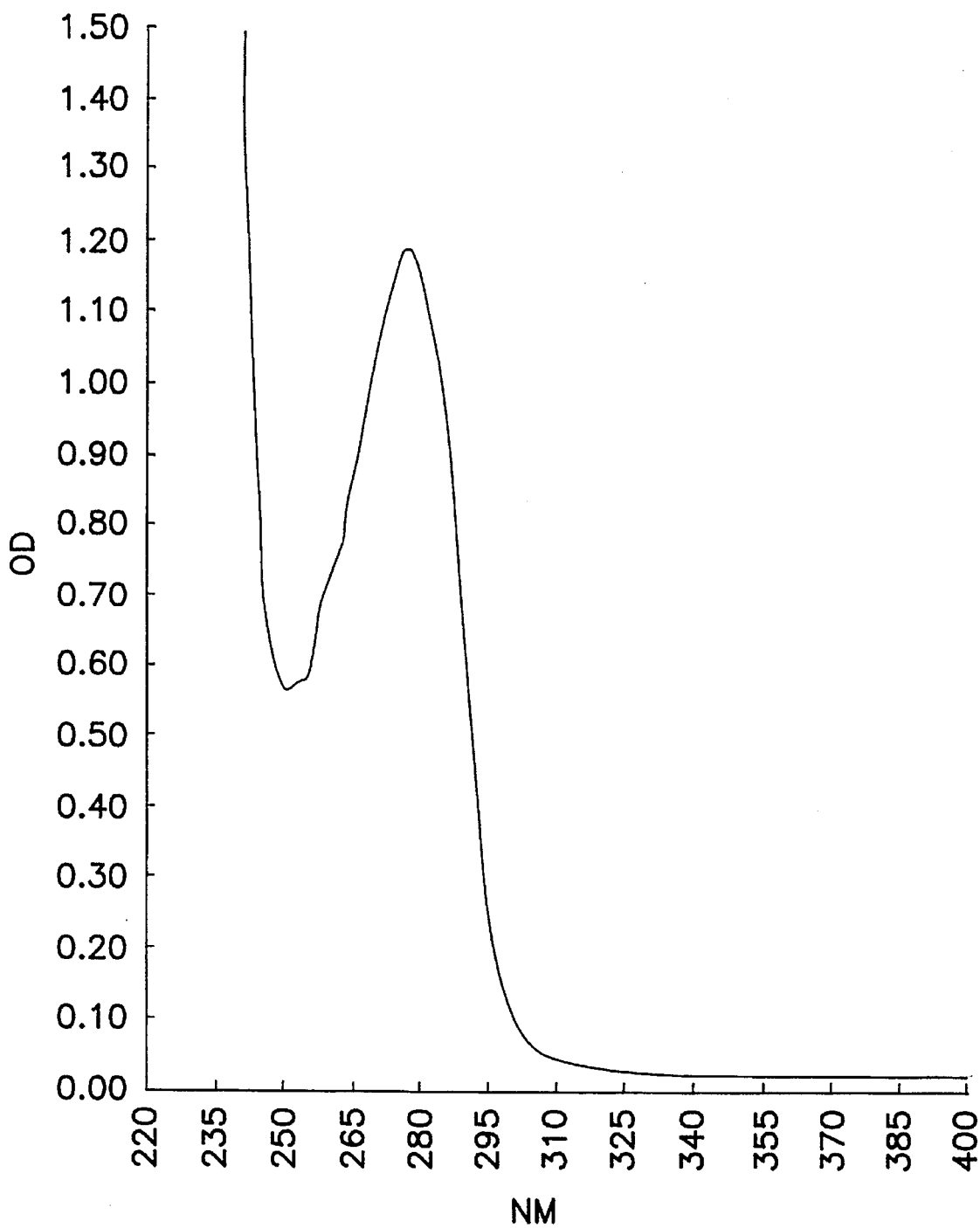

FIGS. 16 and 17: UV spectra for various preparations of albumin: FIG. 16: (1) albumin BCQ759 of Examples B1 and B2; (2) albumin BCQ804LE of Example B5; (3) control albumin (IM). FIG. 17: albumin BCQ835GE of Example B5.

Figure 18:
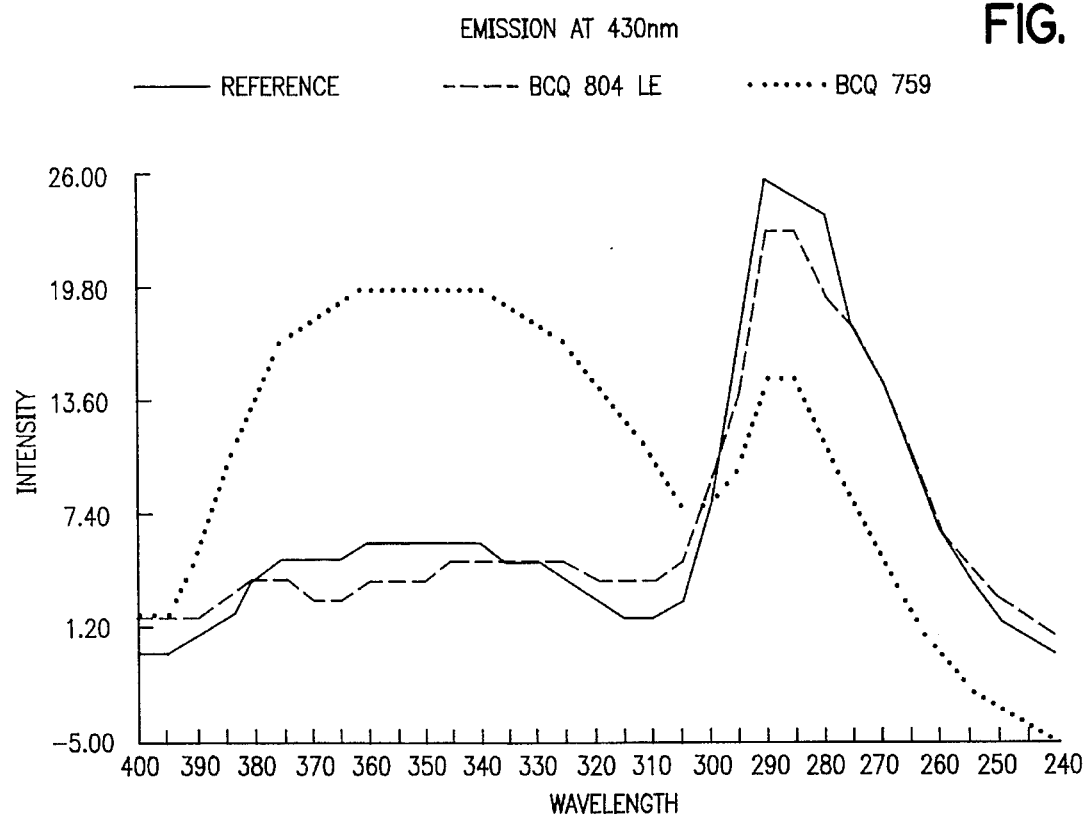
Figure 19:
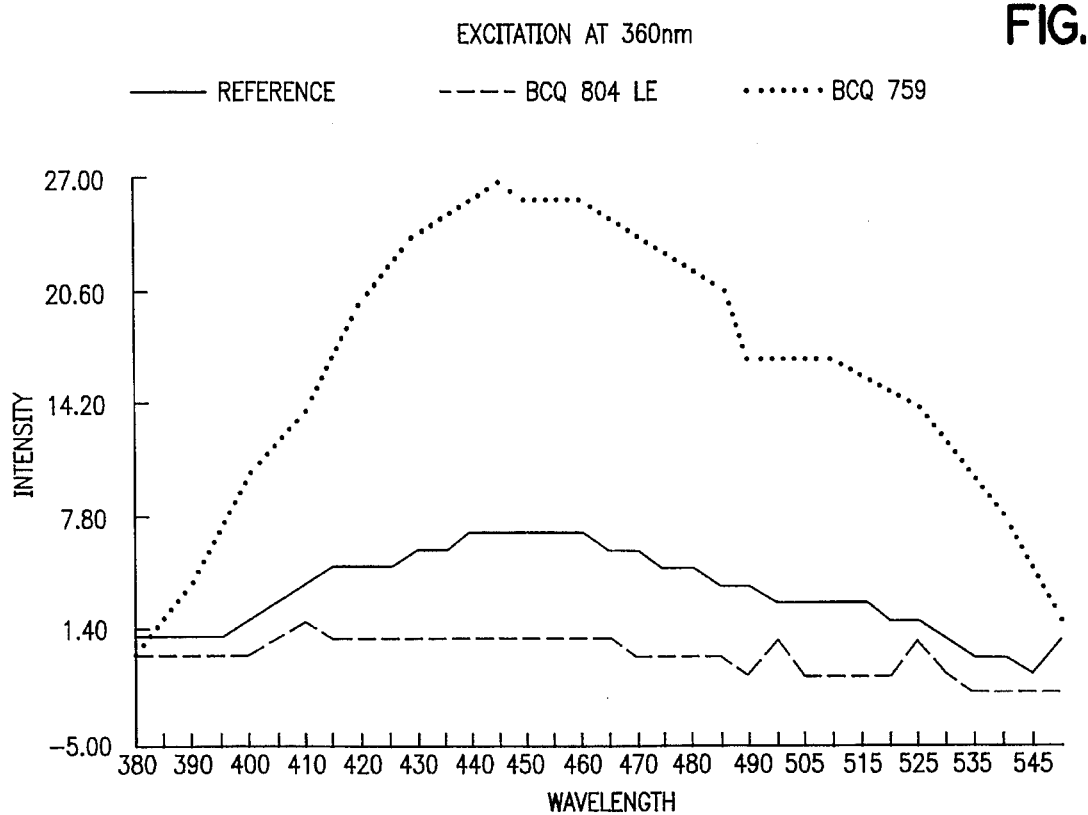

FIGS. 18 and 19: Fluorescence spectra for various preparations of albumin at 430 nm (FIG. 18) and 360 nm (FIG. 19).

GENERAL CLONING TECHNIQUES

The conventional molecular biology methods such as centrifugation of plasmid DNA in cesium chloride— ethidium bromide gradient, digestion with restriction enzymes, gel electrophoresis, electroelution of the DNA fragments from agarose gels, transformation in E. coli, and the like, are described in the literature (Maniatis et al., "Molecular Cloning: a Laboratory Manual", Cold Spring Harbor Laboratory, Cold Spring Harbor, New York, 1986; Ausubel et al., (eds.), "Current Protocols in Molecular Biology", John Wiley & Sons, New York 1987).

Site-directed mutagenesis in vitro by oligodeoxynucleotides is carried out according to the method developed by Taylor et al. (Nucleic Acids Res. 13 (1985) 8749–8764) using the kit distributed by Amersham. The sequencing of nucleotides is carried out according to the dideoxy technique described by Sanger et al. (Proc. Natl. Acad. Sci. U.S.A., 74 (1977) 5463–5467). Enzymatic amplification of specific DNA fragments is carried out by the PCR reaction ("Polymerase-catalyzed Chain Reaction") under the conditions described by Mullis and Faloona (Meth. Enzym., 155 (1987) 335–350), and Saiki et al (Science 230 (1985) 1350–1354), using a "DNA thermal cycler" (Perkin Elmer Cetus) following the recommendations of the manufacturer.

EXAMPLES

A—Construction of human serum albumin expression vectors

1. Construction of a HSA expression vector under the control of a hybrid promoter PGK/GAL: plasmid pYG401.

A human serum albumin expression vector was prepared from the plasmid pYG19 (EP 361 991). The latter comprises the following elements:

the sequence of the plasmid pKD1, which makes pYG19 a multicopy plasmid which is stable and capable of replicating in the yeasts of the genus Kluyveromyces (EP 361 991), a human serum albumin expression cassette containing the structural gene encoding the prepro form under the control of the promoter of the PGK gene of S. cerevisiae;

a bacterial replicon and selectable marker (bla gene conferring the resistance to ampicillin); and, the aph gene conferring the resistance to G418 on yeast.

The vector pYG401 was constructed from the plasmid pYG19 by modification at the level of the human serum albumin expression cassette. In pYG401, the albumin gene is no longer under the control of the promoter of the PGK gene of S. cerevisiae, but under the control of a hybrid promoter between the promoters of the PGK and GAL1/GAL10 genes of S. cerevisiae. This hybrid promoter was obtained by replacing the UAS ("Upstream Activating Sequence") region of the PGK promoter (Stanway et al., Nucl. Acid Res. 15 (1987) 6855) with the UAS region of the GAL1/GAL10 promoter (Johnston and Davies, Mol. Cell. Biol. 4 (1984) 1440; West et al., Mol. Cell. Biol. 4 (1984) 2467).

This hybrid promoter was constructed in the following manner (cf FIG. 1):

The production of the plasmid pYG29 has been described in detail in the application EP 361 991. This plasmid contains the promoter of the PGK gene S. cerevisiae isolated from the plasmid pYG19 in the form of a SalI-HindIII fragment, and cloned into the bacteriophage M13mp18. It was then modified by site-directed mutagenesis in order to introduce the following restriction sites:

1 additional HindIII site in position −25 relative to ATG. The introduction of this site makes it possible to restore, after the various cloning steps, a nucleotide region close to ATG identical to the native region of the PGK promoter. The surrounding of the ATG codon is indeed known to substantially influence the efficiency of the initiation of translation of eucaryotic genes (Kozak, M., Microbiol. Rev. 47 (1983) 1–45;Hamilton, R., Nucl. Acid. Res 15 (1987) 3581–3593).

2 NotI sites on either side of the UAS region.

The UAS of the GAL1/GAL10 promoter was isolated from the plasmid pG1 described by Miyajima et al. (Nucl. Acid. Res 12 (1984) 6397–6414; Cloning Vectors, Pouwels et al., Elsevier (1985) VI-B-ii-2). This plasmid is deposited at ATCC under the number 37305.

The plasmid pG1 contains a fragment of 0.8 kb containing the GAL1/GAL10 promoter of *S. cerevisiae*, inserted into the HindII site of the plasmid pUC8, from which it can be excised in the form of a BamHI-PstI fragment (FIG. 1).

This fragment was excised from pG1, purified and then digested with the enzymes RsaI and AluI, whose respective cleavage sites are localized on either side of the UAS region. A 143 bp fragment was thus isolated by electroelution and then converted to a NotI fragment by adding a linker 5'-GCGGCCGC-3'(SEQ ID NO:7). This fragment was then cloned into the plasmid pYG29, previously digested with NotI.

The resulting plasmid is called pYG32 (FIG. 1).

To obtain the expression vector carrying this hybrid promoter, the SalI-HindIII fragment carrying the hybrid promoter was isolated from pYG32 and ligated to a synthetic HindIII-BstEII adaptor composed of the following 2 complementary strands: 5'-AGC TTT ACA ACA AAT ATA AAA ACA ATG AAG TGG-3' (SEQ ID NO:8) and 5'-GT TAC CCA CTT CAT TGT TTT TAT ATT TGT TGT AA-3' (SEQ ID NO:9) (the transcriptional initiation codon is represented in bold characters). This adaptor reconstitutes the 22 bp situated immediately upstream of the PGK structural gene of *S. cerevisiae*, and comprises the first codons of the gene encoding preproHSA, up to a BstEII site present in the native gene (FIG. 1).

The human albumin expression cassette was then reconstituted by ligating the SalI-BstEII fragment thus obtained carrying the hybrid promoter and the 5' end of the albumin structural gene, to the BstEII-SacI fragment isolated from the plasmid pYG19, carrying the rest of the albumin gene, and the terminator of the PGK gene of *S. cerevisiae* (FIG. 2).

The cassette thus obtained was used to replace the SalI-SacI expression cassette carried by the plasmid pYG19.

The resulting vector is called pYG401 (FIG. 2).

2. Construction of a HSA expression vector under control of the promoter K1ADH4: plasmid pYG132.

2.1 Isolation of the promoter K1ADH4 from *K. lactis*.

The promoter K1ADH4 was obtained by screening a total genomic DNA library for *Kluyveromyces lactis* CBS2359/152 by means of a heterologous probe obtained from the ADH2 gene of *S. cerevisiae*. More specifically, the library was obtained by cloning into the BamHI site of the replacement vector Lambda-L47 the product of a partial digestion with the enzyme Sau3A of DNA of *K. lactis* CBS2359/152. The probe used for the hybridization is a 980 bp EcoRV-BamHI fragment comprising the region encoding the ADH2 structural gene of *S. cerevisiae*, with the exception of the first 70 bp (probe A). This fragment is obtained by enzymatic digestion from a plasmid called pBR322.ADR2.BSa (Williamson et al., Cell 23 (1981) 605–614; Russell et al., J. Biol. Chem. 258 (1983) 2674–2682).

A fragment of about 8 kb was thus isolated and subcloned into the BamHI site of the plasmid pBR322 in order to generate the plasmid p6-4-98 (FIG. 3). The BamHI insert carried by this plasmid was then mapped by means of restriction enzymes, and the promoter region of the K1ADH4 gene was localized on this fragment by differential hybridizations using the probe A as well as a second probe corresponding to the BamHI-EcoRV fragment of about 1100 bp of the plasmid pBR322.ADR2.BSa (probe B).

In a second step, the plasmid p6-4-98 was digested with the enzyme HindIII and a 2.2 kb fragment was isolated. This fragment was then purified by standard techniques and subcloned into the HindIII site of the plasmid pTZ19 in order to generate the plasmid p6-2200-2 (FIG. 3). Analysis of the subcloned fragment reveals that it contains the first 14 codons of the K1ADH4 gene and the region situated upstream thereof, comprising the elements for regulating the expression.

The part between the BglII site and the translational initiation codon ATG (fragment of about 1.2 kb) was sequenced using the chain termination method (Sanger et al., Proc. Nat. Acad. Sci. 74 (1977) 5463).

2.2 Construction of a portable promoter K1ADH4 (BglII-BamHI)

A portable promoter was prepared by inserting into the 2.2 kb HindIII fragment present in the plasmid p6-2200-2 a BamHI restriction site at position −16 relative to the ATG codon of the K1ADH4 gene.

The insertion of this site makes it possible to generate a 1.2 kb BglII-BamHI fragment comprising exclusively the promoter region K1ADH4. It also makes it possible to introduce, downstream of the promoter thus obtained, any gene which it is desired to express.

The BamHI site was introduced at position −16 relative to the site for initiation of translation (ATG) of the K1ADH4 gene by site-directed mutagenesis using the double primer technique (Sambrook, Fritsch, Maniatis, Molecular Cloning Laboratory Manual, Cold Spring Harbor Lab Press, 1989). The sequence of the synthetic oligodeoxynucleotides used for this mutagenesis is given below. The BamHI site generated is underlined, ATG is indicated in italics and the asterisks designate the modified bases compared with the initial sequence. IS=initial sequence; MS=modified sequence.

| | |
|---|---|
| 5'-CTCCCCCACCAACAACACAACATACAA-CACACGCAATGTTCAGATT-1' (IS), | SEQ ID NO:10 |
| 5'-CTCCCCCACCAACAACACAGGATCCAA-CACACGCAATGTTCAGATT-3' (MS), | SEQ ID NO:11 |
| 3'-GAGGGGGTGGTTGTTGTGTCCTAGGT-TGTGTGCGTTACAAGTCTAA-5' (MS), | SEQ ID NO:12 |

The plasmid thus obtained is called pP4–33 (FIG. 3).

2.3 Construction of a human serum albumin (HSA) expression vector:

To construct a human serum albumin expression vector, a derivative of the plasmid pYG404 (Cf EP 361 991) was prepared, containing:

a yeast replicon (practically the whole sequence of the natural plasmid pKD1), the gene encoding the prepro-human albumin (HSA) under the control of the promoter of the LAC4 gene of *K. lactis* and followed by the terminator of the PGK gene of *S. cerevisiae*; the structural gene encoding HSA is preceded by a sequence of 25 nucleotides corresponding to the region directly upstream of the PGK gene of *S. cerevisiae*, the aph gene conferring the resistance to geneticin (G418) on yeast, and a replicon and a selectable marker (bla gene conferring the resistance to ampicillin) for *E. coli*.

This plasmid, called pYG404ΔH, differs from pYG404 only in the destruction of the HindIII site, localized in the aph gene, by site-directed mutagenesis. This modification then made it possible to substitute the LAC4 promoter present in the plasmid pYG404ΔH in the form of a SalI-HindIII fragment by the promoter K1ADH4 also constructed in the form of a SalI-HindIII fragment.

(a) Construction of the plasmid pYG404ΔH (FIGS. 4–7).

In order to carry out the deletion of the HindIII site in the cloning vector pYG404, various subcloning steps were carried out, giving rise to an intermediate construct: pYG72 (FIG. 6). This vector corresponds to the plasmid pKan707 (EP 361 991) in which the SacI fragment containing the URA3 gene has been removed as well as the unique HindIII site present in the aph gene. In Order to carry out the site-directed mutagenesis at this site, the 1.3 kb PstI fragment carrying the aph gene was subcloned from the plasmid pKan707 into the bacteriophage M13mp7 in order to give the vector pYG64 (FIG. 4). The HindIII site was destroyed by site-directed mutagenesis (Cf general cloning techniques) using the following oligodeoxynucleotide: 5'-GAAATG CAT AAG CTC TTG CCA TTC TCA CCG-3' (SEQ ID NO:13), permitting the replacement of the CTT triplet encoding leucine 185 with the triplet CTC. This change does not modify the resulting protein sequence. The plasmid obtained was called pYG65 (FIG. 4). In order to construct the plasmid pYG72, the part containing the bacterial replicon of the vector pKan707 was isolated by digestion with the enzyme EcoRI and recircularization with T4 DNA ligase, generating the intermediate plasmid pYG69. The PstI fragment present in the latter containing the aph gene was then replaced by the equivalent mutated fragment obtained from the plasmid pYG65. This construct was called pYG70 (FIG. 5). The 4.7 kb pKD1 sequence between the EcoRI and SacI sites was then introduced into this vector in order to obtain pYG72 (FIG. 6).

The vector pYG404ΔH was obtained by inserting the expression cassette obtained from the plasmid pYG404 (EP 361 991) in the form of a SalI-SacI fragment at the corresponding sites of pYG72 (FIG. 7).

(b) Construction of a portable promoter K1ADH4 [SalI-HindIII] (FIG. 8).

The promoter K1ADH4 carried on the BglII-BamHI fragment obtained from the plasmid pP4-33 (Cf 2.1.) was modified in the following manner in order to adapt it for use in expression vectors derived from the plasmid pYG404ΔH:

After digestion of the plasmid pP4-33 with the enzymes BglII and BamHI, followed by a treatment with 'Mung Bean' nuclease in order to render the ends blunt, the 1.2 kb fragment carrying the promoter K1ADH4 was isolated from an agarose gel and subcloned into the vector pBC SK+ (Stratagene, La Jolla, Calif., U.S.A.) previously linearized with the enzyme ClaI and treated with 'Mung Bean' nuclease as well as with calf alkaline phosphatase (CIP). The plasmid obtained in this manner (pYG128, FIG. 8) permits the isolation of the promoter K1ADH4 in the form of a 1.2 kb SalI-HindIII fragment.

(c) Construction of the vector pYG132 (FIG. 9).

The digestion of the expression vector pYG404ΔH (Cf 2.3. (a)) with the enzymes SalI and HindIII permits the replacement of the promoter LAC4 with the promoter K1ADH4 described above.

In order to carry out this cloning, the 8.7 kb SalI-HindIII fragment containing the pKD1 part and the selectable markers as well as the 1.9 kb HindIII-HindIII fragment carrying the gene encoding prepro-HSA were isolated from the vector pYG404ΔH and religated in the presence of the 1.2 kb SalI-HindIII fragment obtained from the plasmid pYG128 and carrying the promoter K1ADH4. Two plasmids were obtained in this manner:

pYG131 (FIG. 9), corresponding to a cloning vector permitting the insertion, at the unique HindIII site, of any gene which it is desired to express under the control of the promoter K1ADH4, and pYG132 (FIG. 9), which is identical to the plasmid pYG131 except that it contains the preproHSA gene introduced into the HindIII site.

3. Construction of a HSA expression vector under the control of the prynoter of the LAC4 gene of *K. lactis*: plasmid pYG1023.

3.1. Isolation of the PGK gene from *K. lactis*.

The PGK gene was isolated from *K. lactis* CBS2359 by the screening of a partial genomic library with a heterologous probe corresponding to the N-terminal part of the PGK gene of *S. cerevisiae* (Dobson et al., Nucl. Acid. Res. 10 (1982) 2625–2637). More specifically, the probe used corresponds to the PvuI-EcoRI fragment of 1.3 kb.

In Southern blotting (Southern et al., J. Biol. Chem. 98 (1975) 503), the probe used hybridizes especially to a DNA sequence contained in a 4 kb HindIII-HindIII fragment. This sequence was isolated by colony hybridization by means of the preceding probe. For that, a limited genomic DNA library from the strain CSB2359, consisting of HindIII fragments of between 3 and 5 kb in size, introduced into the HindIII site of the plasmid pUC18, was prepared and screened.

A clone carrying the plasmid pYG600 (FIG. 10) was thus isolated. The sequence of the PGK gene carried by this plasmid has been described by Fournier et al. (Nucl. Acid. Res. 18 (1990) 369).

3.2. Construction of a human serum albumin expression vector carrying the PGK gene of *K. lactis*.

The plasmid pYG70 described in FIG. 5 was modified as follows.

(a) Modification of the restriction sites of the plasmid pYG70 (FIG. 11).

In order to facilitate the subsequent cloning steps, some restriction sites were suppressed from (i) and 2 adaptors were added to (ii and iii) the plasmid pYG70.

(i) Removal of the SphI site.

The plasmid pYG70 was digested with SphI, and the cohesive ends were then removed by digestion in the presence of phage T4 DNA polymerase. After ligation in the presence of ligase, the plasmid pYG70ΔSphI was obtained (see FIG. 11).

(ii) Insertion of the adaptor 1.

The adaptor 1 was obtained by hybridization of the synthetic oligodeoxynucleotides A and B represented in FIG. 12. For that, 2 µg of each oligodeoxynucleotide were incubated in a hybridization buffer qs 20 µl (30 mM Tris-HCl buffer pH 7.5; 30 mM NaCl; 7.5 mM $MgCl_2$; 0.25 mM ATP; 2 mM DTT; 0.2 mM EDTA), and then the temperature was raised to 80° C. for 10 minutes, and brought back slowly to room temperature.

The adaptor thus obtained contains the cleavage sites for the following enzymes: SacI; SalI; MluI; BssHII and SfiI, and makes it possible to remove, during its introduction, the SalI site present in the plasmid pYG70ΔSphI. This adaptor was introduced by ligation into the plasmid pYG70ΔSphI previously digested with the enzymes SalI and SacI.

The plasmid obtained is called pYG70-1.

(iii) Insertion of the adaptor 2.

The adaptor 2 was prepared following the procedure described for the adaptor 1, using the oligodeoxynucleotides C and D described in FIG. 12. This adaptor contains cleavage sites for the following enzymest SfiI; AatII; Sph; NarI and SacI and makes it possible to remove, during its introduction, the EcoRI site present in the plasmid pYG70-1. It was introduced, by ligation, into the plasmid pYG70-1 previously digested with the enzymes EcoRI and SacI, to form the plasmid pYG70-2 (FIG. 11).

(b) Introduction of a human serum albumin expression cassette.

The human serum albumin expression cassette used comprises:

the inducible promoter of the LAC4 gene of *K. lactis*, the structural gene encoding human serum albumin (prepro form), and the terminator of the PGK gene of *S. cerevisiae*.

This cassette was isolated from the plasmid pYG404 (EP 361 991) in the form of a SalI-SacI fragment, and then introduced by ligation into the plasmid pYG70-2 previously digested with the corresponding enzymes.

The plasmid obtained is called pYG70-3 (FIG. 13).

(c) Insertion of the PGK gene of *K. lactis*.

The *K. lactis* PGK gene was isolated from the plasmid pYG600 (FIG. 10), subcloned into the plasmid pYG1002 in order to generate the plasmid pYG1003, and then isolated from the latter in the form of an MluI-BssHII fragment.

The subcloning into pYG1002 made it possible to obtain the *K. lactis* PGK gene free of its promoter, and in the form of an MluI-BssHII fragment.

The plasmid pYG1003 was obtained in the following manner (FIG. 14):

The plasmid pIC20H (Marsh et al., Gene 32 (1984) 481) was digested with BglII and EcoRI so as to introduce the adaptor 3. This adaptor, which provides the EcoRI, BssHII, ClaI, NheI, MluI and BglII sites, was obtained as described above (2.(a) (ii)), by hybridization of the oligodeoxynucleotides E and F (FIG. 12). The resulting plasmid is called pYG1002. The PGK gene of *K. lactis* was introduced into this new plasmid in the form of a ClaI-NheI fragment, derived from the plasmid pYG600. The plasmid obtained is called pYG1003 (FIG. 14).

The MluI-BssHII fragment derived from the plasmid pYG1003 carrying the PGK gene of *K. lactis* was then introduced into the corresponding sites in the plasmid pYG70-3, to generate the plasmid pYG70-4 (FIG. 15).

In this plasmid, the PGK gene of *K. lactis* is henceforth placed under the control of the bidirectional kl promoter of the Killer toxin.

(d) Insertion of the yeast replicon.

The plasmids pYG70-4 (FIG. 15) and pKD1 (EP 361 991) were digested with SphI and ligated together in the presence of ligase. At the end of this ligation, 4 vectors can be obtained, depending on the conformation of the plasmid pKD1 (form A or form B) and the orientation of the part corresponding to the plasmid pYG70-4 relative to pKD1.

One of these constructs was selected and called pYG1023 (FIG. 15). This vector comprises:

an entire sequence of the plasmid pKD1, which makes pYG1023 a multicopy plasmid which is stable and capable of replicating in yeasts and preferably yeasts of the genus Kluyveromyces, a human serum albumin expression cassette containing the structural gene encoding the prepro form under the control of the inducible promoter of the LAC4 gene of *K. lactic*, and of the terminator of the PGK gene of *S. cerevisiae*, a replicon and a selectable marker (bla gene conferring the resistance to ampicillin) for *E. coli*, two selectable markers for the *K. lactis* pgk strain: the mutated aph gene under the control of the bidirectional k1 promoter of the Killer toxin and the PGK gene of *K. lactis* under the control of the same promoter but transcribed divergently compared with the aph gene.

B—Production of human serum albumin via the recombinant route

B1. This example describes a conventional process for the production of recombinant HSA using the yeast *K. lactis* CBS683 transformed with the vector pYG401 (Example A1). This example illustrates the prior art.

The culture was carried out in a 2 liter fermenter at 28° C. in fed-batch mode. Initially, the fermenter contains 0.7 liter of basic medium (glucose 2 g/l, yeast extract 3 g/l, salts). A 50 ml culture in exponential growth phase (inoculated from a frozen suspension) is used to inoculate the fermenter. After a preliminary batch-type growth phase, the additional load (glucose, corn steep, ammonium salts: 40%/13%/7% [w/v]) is added exponentially. After 64 hours of culture, the broth is centrifuged and the supernatent microfiltered on a 2µ membrane. The purification procedure comprises an affinity chromatrography step on Blue Trisacryl (IBF, France) from which the albumin is eluted by a high salt concentration (3.5M NaCl), and then, after concentration and diafiltration, a passage on a Q-sepharose "fast flow" type ion exchanger. The HSA thus purified has a homogeneous band in SDS-PAGE electrophoresis and is indistinguishable from natural albumins taken as reference in numerous tests for biochemical characterization. Yet, a solution of the HSA obtained has a yellow coloration with a colorimetry index i=0.26 which is impossible to remove by a more extensive purification and/or treatments such as the use of activated charcoals, as well as an abnormal fluorescence after excitation at 360 nm (FIGS. 16, 18 and 19).

B2. A batch of recombinant albumin BCQ 759 obtained under the conditions described in Example B1 has a coloration index i=0.26 after purification (FIG. 16). Numerous additional chromatographic trials and physico-chemical treatments do not make it possible to reduce this coloration.

In order to analyse the nature of the binding of this coloration to albumin, a denaturation-renaturation cycle was performed as follows:

50 mg of BCQ 759 are denatured by incubation in 2 ml of 7M guanidine-HCl and 0.3M β-mercaptoethanol. This solution is heated for 1 hour at 100° C. After cooling, 500 µl of denatured rHSA are injected into a TSK 3000SW column equilibrated with 8M urea and 0.3M β-mercaptoethanol in order to remove the small molecules which may be strongly attached (but not covalently) to HSA. The fractions absorbing at 280 nm are dialysed against a 50 mM Tris HCl, 8M urea solution, pH 8.0 overnight under nitrogen and then against 1 liter of renaturing buffer 50 mM Tris HCl , pH 9.5 containing 50 mM NaCl, 1 mM reduced glutathione and 0.1 mM oxidized glutathione under nitrogen for 48 hours. After final dialysis against water, a UV spectrum is produced and a coloration index $i_2$=0.22 is calculated. Under the same conditions, a control placental albumin (Institut Mérieux, i=0.07) gives, after renaturing, $i_2$=0.14. This example clearly demonstrates the essentially covalent nature of binding of the piment to albumin. It is therefore futile to try to significantly decolorize a recombinant albumin by the purification process.

B3. In this example is described a simple experiment which makes it possible to demonstrate that the carbon source iS an essential cause of the development of the coloration.

The control albumin (i=0.07) is incubated in various culture media in an erlen flask without inoculating with yeast. The tested media consist of a basic medium Bo defined as follows:

| | | |
|---|---|---|
| Salts | Ammonium acetate | 7 g/l |
| | $Na_2HPO_4$ | 4.4 g/l |
| | $KH_2PO_4$ | 4 g/l |
| | $MgSO_4, 7H_2O$ | 0.5 g/l |
| | $CaCl_2, 2H_2O$ | 0.1 g/l |
| | $MnSO_4, H_2O$ | 10 mg/l |
| | $ZnSO_4, 7H_2O$ | 100 mg/l |
| | $FeSO_4, 7H_2O$ | 15 mg/l |
| | $AlCl_3, 6H_2O$ | 1 mg/l |
| | $CoCl_2, 6H_2O$ | 2 mg/l |
| | $CuSO_4, 5H_2O$ | 0.13 mg/l |
| | KI | 0.33 mg/l |
| | $H_3BO_3$ | 1.47 mg/l |
| | $Na_2MoO_4$ | 0.67 mg/l |
| Vitamins | Mesoinositol | 2 mg/l |
| | Nicotinic acid | 2 mg/l |
| | Biotin | 2 mg/l |
| | Calcium pantothenate | 2 mg/l |
| Amino acids | L-Glu | 0.6 g/l |
| | L-Phe | 0.15 g/l |
| | DL-Ala | 0.7 g/l |
| | L-Leu | 0.35 g/l |
| | L-Lys, HCl | 0.30 g/l |
| | DL-His, HCl | 0.30 g/l |
| | L-Ile | 0.10 g/l |
| | DL-Met | 0.15 g/l |
| | L-Pro | 0.3 g/l | and of a carbon source:

| | | | |
|---|---|---|---|
| erlen flask | E1: | glucose (microfiltered) | 20 g/l |
| | E2: | lactose | 20 g/l |
| | E3: | control (without carbon source) | |

The three erlen flasks are incubated with HSA at 50 mg/l and stirred at 28° C. for 3 days.

After 3 days, the medium is centrifuged and filtered on a 0.2μ membrane. 5 ml of affinity support Blue Trisacryl M (IBF France) are added and the mixture is stirred gently. After 1 hour, the mother liquors are separated on sintered glass and the albumin eluted with a 3.5M NaCl solution. The eluate is then concentrated and diafiltered with water on a 10 kD ultrafiltration membrane.

A spectrophotometric analysis gives the following results for the coloration index of albumin:

| | | |
|---|---|---|
| erlen flask | E1 | i = 0.16 |
| | E2 | i = 0.12 |
| | E3 | i = 0.09 |
| | control HSA | i = 0.07 |

This example therefore clearly shows that the carbon source induces an increase in the coloration of albumin under the cultural conditions without yeast.

B4. in order to complete the results obtained in the preceding example, the reference albumin was incubated under the same conditions in the presence of:

| | | | |
|---|---|---|---|
| erlen flask | E4 | autoclaved Bo + glucose medium | 20 g/l |
| | E5 | microfiltered Bo + glucose medium | 20 g/l |
| | E6 | microfiltered Bo + sucrose medium | 20 g/l |

After concentration and diafiltration of the medium in order to remove the small molecules, the coloration index was determined in UV:

| | |
|---|---|
| E4 | i = 0.22 |
| E5 | i = 0.15 |
| E6 | i = 0.14 |

B5. In order to verify the conclusions obtained in the preceding examples during a real culture, the coloration of the recombinant albumin produced in an erlen flask by the yeast *K. lactis* was analysed.

a) Strain *K. lactis* pgk CBS 295.91 transformed with the vector pYG1023 described in Example A3:

| | |
|---|---|
| Erlen flasks: | E7 = Bo + lactose 10 g/l + ethanol 10 g/l |
| | E8 = Bo + lactone 20 g/l |
| | E9 = Bo + microfiltered glucose 20 g/l |
| | E10 = Bo + lactose 10 g/l + glucose 10 g/l |

The recombinant albumin produced after 72 hours of culture in batch mode, in 250 ml erlenmeyer flasks at 28° C., is purified on a Mono Q HRS/5 anion-exchange column (Pharmacia) and treated with activated charcoal in order to remove the coloration which is not covalently attached to the protein. The results obtained after UV analysis are the following:

| | | |
|---|---|---|
| E7 | i = 0.11 | BCQ 804 LE (see Figures 16, 18 and 19) |
| E8 | i = 0.14 | BCQ 804 L |
| E9 | i = 0.17 | BCQ 804 G |
| E10 | i = 0.15 | BCQ 804 LG | b) Strain *K. lactis* CBS 293.91 transformed with the vector pYG132 described in Example A2: Erlen flask: E11=Bo+glycerol 10 g/l+ethanol 10 g/l Under the same conditions as above, the recombinant albumin produced gives, after simple purification on Mono Q, a coloration index i=0.09 (BCQ 835 GE): see FIG. 17.

We claim:

1. A process for preparing human serum albumin having a colorimetry index of less than 0.2 in a Kluyveromyces host consisting essentially of:

introducing an exogenous DNA encoding human serum albumin into the host, culturing the host in a defined medium consisting essentially of basic medium $B_0$ and at least one carbon source selected from the group consisting of ethanol, glycerol, sorbitol, sucrose, acetates, lactates, disaccharides having a 1–4 type glycoside bond, and microfiltered glucose, recovering the human serum albumin produced.

2. The process of claim 1 wherein the medium comprises at least one carbon source selected from the group consisting of maltose, cellobiose, and lactose.

3. The process of claim 1 wherein the carbon sources are lactose and ethanol.

4. The process of claim 1 wherein the carbon sources are glycerol and ethanol.

5. The process of claim 1 wherein the carbon sources are lactose and glucose.

6. The process of claim 1 wherein the carbon source is lactose.

7. The process of claim 1 wherein the carbon source is microfiltered glucose.

8. The process according to claim 1, characterized in that the exogenous DNA is selected from the group consisting of cDNA sequences, genomic DNA sequences and hybrid sequences.

9. The process according to claim 1, characterized in that the HSA is secreted into the culture medium.

10. The process of claim 8 characterized in that the DNA is a cDNA.

11. The process according to claim 1, characterized in that the medium comprises at least two carbon sources selected from the group consisting of ethanol, glycerol, sorbitol, sucrose, acetates, lactates, disaccharides having a 1–4 type glycoside bond, and microfiltered glucose.

* * * * *

SEQUENCE LISTING ( 1 ) GENERAL INFORMATION:

( i i i ) NUMBER OF SEQUENCES: 13

( 2 ) INFORMATION FOR SEQ ID NO:1:

( i ) SEQUENCE CHARACTERISTICS:
        ( A ) LENGTH: 37 base pairs
        ( B ) TYPE: nucleic acid
        ( C ) STRANDEDNESS: single
        ( D ) TOPOLOGY: linear ( i i ) MOLECULE TYPE: other nucleic acid ( v i i ) IMMEDIATE SOURCE:
        ( B ) CLONE: adaptor 1-oligonucleotide A ( x i ) SEQUENCE DESCRIPTION: SEQ ID NO:1:

CGTCGACACG CGTGCGCGCC CGCGGCCAAT GGGGCCC    37

( 2 ) INFORMATION FOR SEQ ID NO:2:

( i ) SEQUENCE CHARACTERISTICS:
        ( A ) LENGTH: 45 base pairs
        ( B ) TYPE: nucleic acid
        ( C ) STRANDEDNESS: single
        ( D ) TOPOLOGY: linear ( i i ) MOLECULE TYPE: other nucleic acid ( v i i ) IMMEDIATE SOURCE:
        ( B ) CLONE: Adaptor 1-oligonucleotide B ( x i ) SEQUENCE DESCRIPTION: SEQ ID NO:2:

TCGAGGGCCC CATTGGCCGC GGGCGCGCAC GCGTGTCGAC GAGCT    45

( 2 ) INFORMATION FOR SEQ ID NO:3:

( i ) SEQUENCE CHARACTERISTICS:
        ( A ) LENGTH: 41 base pairs
        ( B ) TYPE: nucleic acid
        ( C ) STRANDEDNESS: single
        ( D ) TOPOLOGY: linear ( i i ) MOLECULE TYPE: other nucleic acid ( v i i ) IMMEDIATE SOURCE:
        ( B ) CLONE: Adaptor 2-oligonucleotide C ( x i ) SEQUENCE DESCRIPTION: SEQ ID NO:3:

AATTAGGCCA ATGGGGCCGA CGTCGCATGC GGCGCCGAGC T    41

( 2 ) INFORMATION FOR SEQ ID NO:4:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( i i ) MOLECULE TYPE: other nucleic acid ( v i i ) IMMEDIATE SOURCE:
        ( B ) CLONE: Adaptor 2-oligonucleotide D ( x i ) SEQUENCE DESCRIPTION: SEQ ID NO:4:

CGGCGCCGCA TGCGACGTCG GCCCCATTGG CCT    33

( 2 ) INFORMATION FOR SEQ ID NO:5:

( i ) SEQUENCE CHARACTERISTICS:
        ( A ) LENGTH: 41 base pairs
        ( B ) TYPE: nucleic acid
        ( C ) STRANDEDNESS: single
        ( D ) TOPOLOGY: linear ( i i ) MOLECULE TYPE: other nucleic acid ( v i i ) IMMEDIATE SOURCE:
(B) CLONE: Adaptor 3-oligonucleotide E ( x i ) SEQUENCE DESCRIPTION: SEQ ID NO:5:

AATTCCCCGC GCGCCCATCG ATCCGCTAGC CCACGCGTCC A                      41

(2) INFORMATION FOR SEQ ID NO:6:

( i ) SEQUENCE CHARACTERISTICS:
(A) LENGTH: 41 base pairs
(B) TYPE: nucleic acid
(C) STRANDEDNESS: single
(D) TOPOLOGY: linear ( i i ) MOLECULE TYPE: other nucleic acid ( v i i ) IMMEDIATE SOURCE:
(B) CLONE: Adaptor 3-oligonucleotide F ( x i ) SEQUENCE DESCRIPTION: SEQ ID NO:6:

GATCTGGACG CGTGGGCTAG CGGATCGATG GGCGCGCGGG G                      41

(2) INFORMATION FOR SEQ ID NO:7:

( i ) SEQUENCE CHARACTERISTICS:
(A) LENGTH: 8 base pairs
(B) TYPE: nucleic acid
(C) STRANDEDNESS: single
(D) TOPOLOGY: linear ( i i ) MOLECULE TYPE: other nucleic acid ( x i ) SEQUENCE DESCRIPTION: SEQ ID NO:7:

GCGGCCGC                                                            8

(2) INFORMATION FOR SEQ ID NO:8:

( i ) SEQUENCE CHARACTERISTICS:
(A) LENGTH: 33 base pairs
(B) TYPE: nucleic acid
(C) STRANDEDNESS: single
(D) TOPOLOGY: linear ( i i ) MOLECULE TYPE: other nucleic acid ( x i ) SEQUENCE DESCRIPTION: SEQ ID NO:8:

AGCTTTACAA CAAATATAAA AACAATGAAG TGG                               33

(2) INFORMATION FOR SEQ ID NO:9:

( i ) SEQUENCE CHARACTERISTICS:
(A) LENGTH: 34 base pairs
(B) TYPE: nucleic acid
(C) STRANDEDNESS: single
(D) TOPOLOGY: linear ( i i ) MOLECULE TYPE: other nucleic acid ( x i ) SEQUENCE DESCRIPTION: SEQ ID NO:9:

GTTACCCACT TCATTGTTTT TATATTTGTT GTAA                              34

(2) INFORMATION FOR SEQ ID NO:10:

( i ) SEQUENCE CHARACTERISTICS:
(A) LENGTH: 46 base pairs
(B) TYPE: nucleic acid
(C) STRANDEDNESS: single
(D) TOPOLOGY: linear ( i i ) MOLECULE TYPE: other nucleic acid ( x i ) SEQUENCE DESCRIPTION: SEQ ID NO:10:

CTCCCCCACC AACAACACAA CATACAACAC ACGCAATGTT CAGATT    46

( 2 ) INFORMATION FOR SEQ ID NO:11:

( i ) SEQUENCE CHARACTERISTICS:
        ( A ) LENGTH: 46 base pairs
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:11:

CTCCCCCACC AACAACACAG GATCCAACAC ACGCAATGTT CAGATT    46

( 2 ) INFORMATION FOR SEQ ID NO:12:

( i ) SEQUENCE CHARACTERISTICS:
        ( A ) LENGTH: 46 base pairs
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:12:

AATCTGAACA TTGCGTGTGT TGGATCCTGT GTTGTTGGTG GGGGAG    46

( 2 ) INFORMATION FOR SEQ ID NO:13:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:13:

GAAATGCATA AGCTCTTGCC ATTCTCACCG    30